United States Patent
Wegner et al.

(10) Patent No.: US 10,155,058 B2
(45) Date of Patent: Dec. 18, 2018

(54) USE OF FLUORESCENT POLYMERS IN MARKING COMPOSITIONS FOR THE DIAGNOSTIC DETERMINATION OF CLEANING PERFORMANCE

(71) Applicant: Ecolab USA Inc., St. Paul, MN (US)

(72) Inventors: Joseph Wegner, Falcon Heights, MN (US); Erin Brown, Hager City, WI (US); Jeffery Atkins, Aurora, IL (US); Paul Zinn, Oswego, IL (US); Robert Walicki, Oak Park, IL (US); Lanhua Hu, Woodridge, IL (US)

(73) Assignee: Ecolab USA Inc., St. Paul, MN (US)

( * ) Notice: Subject to any disclaimer, the term of this patent is extended or adjusted under 35 U.S.C. 154(b) by 0 days.

(21) Appl. No.: 15/829,006

(22) Filed: Dec. 1, 2017

(65) Prior Publication Data

US 2018/0085483 A1    Mar. 29, 2018

Related U.S. Application Data

(63) Continuation of application No. 15/456,903, filed on Mar. 13, 2017, now Pat. No. 9,867,895, which is a continuation of application No. 14/320,881, filed on Jul. 1, 2014, now Pat. No. 9,624,423.

(51) Int. Cl.

| | |
|---|---|
| A61L 2/28 | (2006.01) |
| C08F 220/06 | (2006.01) |
| G01N 33/22 | (2006.01) |
| C09K 11/02 | (2006.01) |
| C09K 11/06 | (2006.01) |
| A61L 2/18 | (2006.01) |
| C09B 69/10 | (2006.01) |
| G01N 31/22 | (2006.01) |

(52) U.S. Cl.
CPC ............................ *A61L 2/28* (2013.01); *A61L 2/18* (2013.01); *C08F 220/06* (2013.01); *C09B 69/10* (2013.01); *C09K 11/025* (2013.01); *C09K 11/06* (2013.01); *G01N 31/226* (2013.01); *C09K 2211/1416* (2013.01); *C09K 2211/1433* (2013.01); *C09K 2211/1466* (2013.01)

(58) Field of Classification Search
CPC .... G01N 21/64; G01N 31/226; C08K 5/0041; C08L 23/00; A61L 2/28; A61L 2/18; C08F 270/06; C09K 11/06; C09K 2211/1415; C09K 2211/1433; C09K 2211/1466; C09K 11/025; C09K 11/02; C09K 11/08; C09B 69/10

See application file for complete search history.

(56) References Cited

U.S. PATENT DOCUMENTS

| | | |
|---|---|---|
| 2,982,749 A | 5/1961 | Friedrich et al. |
| 3,284,393 A | 11/1966 | Vanderhoff et al. |
| 3,734,873 A | 5/1973 | Anderson et al. |
| 3,888,863 A | 6/1975 | Troster |
| 4,929,655 A | 5/1990 | Takeda et al. |
| 5,006,590 A | 4/1991 | Takeda et al. |
| 5,378,784 A | 1/1995 | Fong et al. |
| 5,597,858 A | 1/1997 | Ramesh et al. |
| 5,597,859 A | 1/1997 | Hurlock et al. |
| 5,735,940 A | 4/1998 | Coller |
| 6,312,644 B1 | 11/2001 | Moriarty et al. |
| 6,358,746 B1 | 3/2002 | Moriarty et al. |
| 6,645,428 B1 | 11/2003 | Morris et al. |
| 7,148,351 B2 | 12/2006 | Morris et al. |
| 7,601,789 B2 | 10/2009 | Morris et al. |
| 7,718,395 B2 | 5/2010 | Carling |
| 7,780,453 B2 | 8/2010 | Carling |
| 7,785,109 B2 | 8/2010 | Carling |
| 7,875,720 B2 | 1/2011 | Morris et al. |
| 7,943,058 B2 | 5/2011 | Hills et al. |
| 8,084,410 B2 | 12/2011 | Carling |
| 8,308,198 B2 | 11/2012 | Udagawa et al. |
| 8,435,933 B2 | 5/2013 | Carling |
| 8,519,360 B2 | 8/2013 | Schoening et al. |
| 8,639,527 B2 | 1/2014 | Rensvold et al. |
| 8,835,874 B2 | 9/2014 | Burnes et al. |
| 2006/0254985 A1 | 11/2006 | Morris et al. |
| 2012/0085931 A1 | 4/2012 | Burns et al. |
| 2013/0252867 A1 | 9/2013 | Carling |
| 2014/0183140 A1 | 7/2014 | Atkins et al. |

FOREIGN PATENT DOCUMENTS

| | | |
|---|---|---|
| EP | 0657478 A2 | 6/1995 |
| EP | 0630909 B1 | 10/1998 |
| WO | 02/066483 | 8/2002 |
| WO | 2013/025332 A1 | 2/2013 |
| WO | 2014/009445 | 1/2014 |

OTHER PUBLICATIONS

Peters et al., "Benzo[k,l], xanthene-3,4-dicarboximides and benzimidazoxanthenoisoquinolinones—yellow and orange dyes for synthetic-polymer fibres", Journal of the Society of Dyers and Colourists, 1989, 105: 29-35.

Hunkeler et al., "Mechanism, Kinetics and Modelling of the Inverse-Microsuspension Homopolymerization of Acrylamide", Polymer (1989), 30(91): 127-142.

Hunkeler et al., "Mechanism, Kinetics and Modelling of Inverse-Microsuspension Polymerization: 2. Copolymerization of Acrylamide with Quaternary Ammonium Cationic Monomers", Polymer (1991), 32(14): 2626-2640.

McCutcheon's Emulsifiers & Detergents, North American Edition, 2000, vol. 1, pp. 214-228.

Sitzlar et al., "An Environmental Disinfection Odyssey: Evaluation of Sequential Interventions to Improve Disinfection of Clostridium difficile Isolation Rooms", Infection Control and Hospital Epidemiology, 2013, 34(5): 459-465.

(Continued)

Primary Examiner — David Porta
Assistant Examiner — Faye Boosalis
(74) Attorney, Agent, or Firm — Merchant & Gould P.C.

(57) ABSTRACT

The present invention generally relates to fluorescent marking compositions and their use to determine whether a surface has been cleaned. More particularly, the marking compositions comprise fluorescent polymers.

46 Claims, No Drawings

(56) References Cited

OTHER PUBLICATIONS

Weber et al., "Understanding and Preventing Transmission of Healthcare-Associated Pathogens Due to the contaminated Hospital Environment", Infection Control and Hospital Epidemiology, 2013, 34(5): 449-452.
Zhang et al., "Design strategies for fluorescent biodegradable polymeric biomaterials", J. Mater. Chem. B, 2013, 1: 132-148.
International Search Report and Written Opinion issued for PCT/US2015/038869, dated Oct. 16, 2015, 18 pages.
Ragan et al., "Use of Audit and Feedback with Fluorescent Targeting to Achieve Rapid Improvements in Room cleaning in the Intensive Care Unit and Ward Settings," American Journal of Infection Control, 2012, pp. 284-286.
Extended European Search Report for Application No. 15815738.8, dated Jan. 26, 2018.
Ragan et al., "Use of audit and feedback with fluorescent targeting to achieve rapid improvements in room cleaning in the intensive care unit and ward settings," American Journal of Infection Control, vol. 40, No. 3, (Apr. 30, 2012).

USE OF FLUORESCENT POLYMERS IN MARKING COMPOSITIONS FOR THE DIAGNOSTIC DETERMINATION OF CLEANING PERFORMANCE

CROSS-REFERENCE TO RELATED APPLICATIONS

This application is a continuation of U.S. application Ser. No. 15/456,903, filed Mar. 13, 2017, which is a continuation application of U.S. application Ser. No. 14/320,881, filed Jul. 1, 2014, now U.S. Pat. No. 9,624,423 the entireties of which are hereby incorporated by reference.

FIELD OF THE INVENTION

The present invention generally relates to fluorescent marking compositions and their use to determine whether a surface has been cleaned. More particularly, the marking compositions comprise fluorescent polymers.

BACKGROUND OF THE INVENTION

A nosocomial infection or hospital acquired infection (HAI) is an infection acquired in a healthcare facility by a patient admitted for some reason other than that specific infection. HAIs can be acquired in any setting in which healthcare is delivered, including acute care hospitals, ambulatory care settings, and long-term care facilities, such as nursing homes and skilled nursing facilities. Although certain individuals, such as the critically ill, the elderly, young children, and those with compromised immune systems are at greater risk, no patient is immune from the risk of acquiring an infection during a doctor visit or hospital stay.

The pathogens causing significant nosocomial problems include MRSA (methicillin-resistant *Staphylococcus aureas*), VRE (vancomycin-resistant *Enterococcus*), and *Clostridium difficile* (*C. difficile*). Their importance derives from a combination of resistance to presently available treatments and an ability to rapidly spread in the environment around hospitalized patients. MRSA causes skin and wound infections, pneumonia, and bloodstream infections. VRE is present in bowel and urinary tract infections. *C. difficile* is also present in bowel infections and presents as severe diarrhea. For each of these pathogens, control with present antibiotics is problematic, if not impossible. The Center for Disease Control (CDC) estimates that in the United States, at least 2 million people become infected with bacteria that are resistant to antibiotics and at least 23,000 people die as a direct result of these infections. Most deaths related to antibiotic resistance happen in healthcare settings such as hospitals and nursing homes.

Guidelines for prevention of nosocomial infection include the observance of aseptic techniques, frequent hand washing between patients, the use of single-use disposable items, patient isolation, and improved air filtration. In addition, high quality cleaning and disinfection of all patient-care areas is important, especially surfaces close to the patient. Contaminated environmental surfaces provide an important potential source for transmission of healthcare associated pathogens, because some pathogens can survive for long periods of time. Bacterial spores of *C. difficile*, for example, are capable of surviving for up to five months in healthcare facilities.

In view of the above, there is a need to assess cleaning compliance in hospitals, long-term care facilities and other healthcare settings. One such method is a fluorescent marking system to assess the thoroughness of cleaning of environmental surfaces, particularly those designated "high touch objects" (HTOs) by the CDC. In this method, a translucent targeting solution containing a chemical marker that fluoresces under UV light can be applied to HTOs. The dried marking solution is subsequently removed by moistening with a spray disinfectant and wiping with a damp cloth. A hand-held UV light is used to determine whether the marked HTOs in the room have been cleaned.

Use of fluorescent marking systems to audit cleaning efficiency is compromised, however, when the fluorescent mark is not thoroughly removed in the cleaning process. It has been found that current products which use small molecule optical brighteners as fluorophores leave a "ghost" mark under ultraviolet light that cannot be further scrubbed off the surface. Typical optical brighteners have high affinity for surfaces, which becomes problematic on older surfaces, highly porous surfaces, and surfaces cleaned with oxidizing agents (e.g. bleach, peroxide). The presence of pores, scratches, nicks, pitting, and etching in the environmental surface makes it more difficult to completely remove the optical brightener from the surface. Accordingly, there is a need to develop fluorescent marking compositions that do not leave a residue after cleaning.

SUMMARY OF THE INVENTION

A fluorescent marking composition is provided which comprises a water-dispersible fluorescent polymer derived from polymerization of one or more polymerizable monomer units and one or more polymerizable non-fluorescent monomer units, a solvent, and a thickener. The polymer has a weight average molecular weight of 2 to 2000 kDa, and has a light absorption spectrum in the range of about 310 to about 400 nm and a light emission spectrum in the range of about 400 to about 750 nm.

A method of determining whether a location has been cleaned is also provided. The method comprises applying a fluorescent marking composition to a location on an environmental surface, and determining if any of the fluorescent polymer remains on the location after one or more opportunities to clean the environmental surface.

Another method of determining whether a location has been cleaned is also provided. The method comprises applying a fluorescent marking composition comprising a solvent and a water-dispersible fluorescent polymer derived from co-polymerization of one or more polymerizable fluorescent monomer units and one or more polymerizable non-fluorescent monomer units to a location on an environmental surface; and determining if any of the fluorescent polymer remains on the location after one or more opportunities to clean the environmental surface.

A kit is also provided. The kit comprises the fluorescent marking composition, a dispenser for dispensing the composition or an applicator for applying the composition to a surface, and optionally a UV light emitting light source.

Other objects and features will be in part apparent and in part pointed out hereinafter.

DETAILED DESCRIPTION

The compositions of the present invention can be used as fluorescent markers for cleaning processes, and are particularly suitable for healthcare settings. The compositions are stable, low foaming, quickly dried, easily removed, and have a viscosity that allows for a broad range of applications.

These compositions form a film that is difficult to see under normal conditions and is not easily removed by incidental contact. The film deposited on the environmental surface fluoresces under ultraviolet light and can be easily visualized by inspection with a hand held UV light emitting light source, such as a UV flashlight. The film comprising the fluorescent marker is removed by chemicals typically used to clean and disinfect environmental surfaces in hospitals, such as sodium hypochlorite, peracetic acid solutions, peroxide solutions, and quaternized ammonium compound disinfectants. The compositions are unique in that they do not leave a residue or "ghost" mark when the composition is removed during such cleaning processes.

The compositions of the present invention comprise fluorescent polymers and present an improvement over prior art formulations comprising small molecule optical brighteners. Conventional formulations can leave a "ghost" mark or faint outline where they were applied. This is especially true for when such conventional formulations are applied to older surfaces, porous surfaces, and surfaces that had been previously cleaned with oxidizing agents.

Incorporating the fluorophore into the fluorescent polymer appears to improve the removal of the composition from a surface so that it does not leave a residue or "ghost" mark. Typically fluorophores are large organic molecules that exhibit high surface substantivity. Substantivity is advantageous for applications such as printing or laundry where deposition of the fluorophore is desired. However, in the case of a removable marking gel, the highly substantive nature of the fluorophore has negative consequence to removal from a surface, especially a surface containing pores, scratches, pit marks and other surface imperfections. While not wanting to be bound by any particular theory, it is thought that contact between the fluorophore bound polymer composition and the solid surface can result in adsorption of polymer, but that the size of the polymer prevents it from depositing into pores, scratches, pit marks, and other surface imperfections. Further, the solubility of the polymer in water also aids in removal of the fluorophore from the surface when a cleaning or disinfecting solution is applied to a surface via a microfiber, cloth, sponge, mop, wipe, high pressure spray, or other form of mechanical cleaning.

The compositions can be formulated to have a viscosity which is suitable for application through a foam applicator pad or felt tipped pad such as those found on highlighter markers. Conventional formulations are often too viscous for this type of application, and result in a thick glob when dabbed onto a surface. The glob dries to a rough, sticky solid which is clearly visible where applied. In contrast, the disclosed compositions are low foaming and quick drying and do not leave any rough or sticky residue on the surface. Conversely, if the composition is not sufficiently viscous, it can run down a vertical surface. This is of importance on surfaces including, but not limited to, light switches, rounded bath rails, mirrors, door handles, hand rails, touch screen monitors, and doors where applied product could potentially run into, or onto, unwanted areas.

The fluorescent marking compositions of the invention comprise a water-soluble dispersible fluorescent polymer derived from polymerization of one or more polymerizable fluorescent monomer units and one or more polymerizable non-fluorescent monomer units, a solvent, and a thickener. The compositions can further comprise other additives such as a surfactant, a preservative, a pH adjusting agent, or a combination thereof, as discussed further below.

The composition can be a concentrate that is diluted to a desired concentration range before use. Alternatively, the composition can be "ready to use" and is provided in the desired applicator at the desired use concentration. When the composition is a ready to use formulation, the composition comprises from about from about 1 to about 30 wt. % of a fluorescent polymer; from about 60 to about 99 wt. % of a solvent; and from about 0.05 to about 1 wt. % of a thickener. Preferably, the ready to use composition comprises from about 4 to about 25 wt. % of a fluorescent polymer; from about 50 to about 95 wt. % of a solvent; and from about 0.1 to about 0.4 wt. % of a thickener. More preferably, the ready to use composition comprises from about 8 to about 16% of a fluorescent polymer; from about 67 to about 91 wt. % of a solvent; from about 0.1 to about 0.4 wt. % of the thickener; from about 0.1 to about 0.7 wt. % of a preservative; and an optional pH adjusting agent.

The "ready to use" composition can comprise a surfactant. The composition comprises from about from about 1 to about 30 wt. % of a fluorescent polymer; from about 60 to about 99 wt. % of a solvent; from about 0.05 to about 1 wt. % of a thickener, and from about 0.05 to about 10 wt. % of a surfactant. Preferably, the ready to use composition comprises from about 4 to about 25 wt. % of a fluorescent polymer; from about 50 to about 95 wt. % of a solvent; from about 0.1 to about 0.4 wt. % of a thickener, and from about 0.5 to about 10 wt. % of a surfactant. More preferably, the ready to use composition comprises from about 8 to about 16% of a fluorescent polymer; from about 67 to about 91 wt. % of a solvent; from about 0.1 to about 0.4 wt. % of the thickener; from about 1 to about 6 wt. % of a surfactant; from about 0.1 to about 0.7 wt. % of a preservative; and an optional pH adjusting agent.

When the composition is in concentrated form, the weight ratio of the fluorescent polymer to surfactant, fluorescent polymer to thickener, or other relative proportions of ingredients will remain the same as in the ready-to-use composition, but the composition will contain a lesser amount of solvent.

Fluorescent Monomers

The polymerizable fluorescent monomers used to prepare the fluorescent polymers of the composition include, but are not limited to, compounds having the structure (I) to (IX), shown as follows.

The fluorescent monomers can have structure (I), (II), or (III):

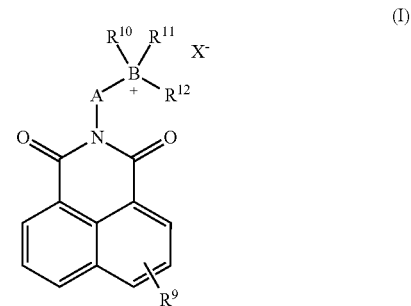

(I)

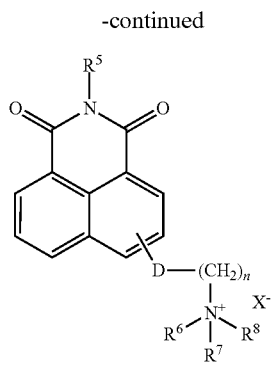

(II)

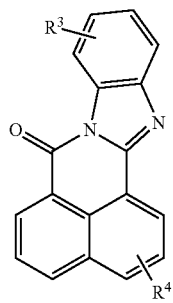

(III)

wherein:
n is an integer from 1 to 10;
A is alkyl, alkoxyalkyl, alkylamidoalkyl, aryl, or is absent; with the proviso that when A is absent, E is nitrogen and E is bonded directly to the imide nitrogen;
E is sulfur or nitrogen with the proviso that when E is sulfur, only one of $R_{10}$ or $R_{11}$ is present;
D is oxygen, nitrogen, sulfur or is absent, with the proviso that when D is absent, $(CH_2)_{11}$ is bonded directly to a carbon on the ring;
$R^3$ and $R^4$ are each independently sulfonic acid or a salt thereof, carboxylic acid or a salt thereof, allyloxy or vinylbenzyloxy, with the proviso that when one of $R^3$ or $R^4$ is sulfonic acid or a salt thereof or carboxylic acid or a salt thereof, the other must be allyloxy or vinylbenzyloxy;
$R^5$ is alkyl, alkylamino, hydroxyalkyl or allyl;
$R^6$ and $R^7$ are each independently alkyl;
$R^8$ is allyl, alkyl, vinylbenzyl or 2-hydroxy-3-allyloxypropyl;
$R^9$ is hydrogen, alkyl, alkoxy, halogen, sulfonic acid or a salt thereof, phosphonic acid or a salt thereof, dialkylamino, allyloxy or vinylbenzyloxy;
$R^{10}$ and $R^{11}$ are each independently alkyl;
$R^{12}$ is allyl, 2-hydroxy-3-allyloxypropyl, vinylbenzyl, 3-methacrylamidopropyl, 3-acrylamidopropyl, 2-acryloxyethyl or 2-methacryloxyethyl; and
$X^-$ is an anion.

Monomers having structures (I), (II), or (III) can be synthesized by reacting a substituted or non-substituted naphthalic anhydride with a primary amine. The amine can be aliphatic, substituted aliphatic, vinyl, or a diamine such as a 1,2-diamino-substituted aromatic compound or hydrazine. Materials required for these syntheses are commercially available and can be obtained, for example, from Sigma-Aldrich. To impact water solubility, the resulting moieties can be quaternized to produce a cationic charge on the fluorescent molecule. Polymerizable moieties can be introduced through substitution on the aromatic ring or during quaternization or imidization.

The fluorescent monomer having structure (I) can be 4-methoxy-N-(3-N',N'-dimethylaminopropylnaphthalimide, vinyl benzyl chloride quaternary salt ($R^9$ =-OMe, A=—$(CH_2)_3$—, B=N, $R^{10}$ and $R^{11}$=Me, $R^{12}$=4-vinylbenzyl, X=Cl, wherein OMe is methoxy).

The fluorescent monomer having structure (I) can be 4-methoxy-N-(3-N',N'-dimethylaminopropylnaphthalimide, allyl chloride quaternary salt ($R^9$=-OMe, A=—$(CH_2)_3$—, B=N, $R^{10}$ and $R^{11}$=Me, $R^{12}$=allyl, X=Cl wherein OMe is methoxy).

The fluorescent monomer having structure (I) can be 4-methoxy-N-(3-N',N'-dimethylaminopropylnaphthalimide, 2-hydroxy-3-allyloxypropyl quaternary salt ($R^9$=—OMe, A=—$(CH_2)_3$—, B=N, $R^{10}$ and $R^{11}$=Me, $R^{12}$=—[$CH_2$CH(OH)$CH_2$O$CH_2$CH=$CH_2$], X=OH, wherein OMe is methoxy). For purposes of this application, this monomer is referred to as "BRT1".

The fluorescent monomer having structure (II) can be N-allyl-4-(2-N',N'-dimethylaminoethoxy)naphthalimide, methyl sulfate quaternary salt (D=O, n=2, $R^5$=allyl, $R^6$ and $R^7$ and $R^8$=Me, and X=—OS(O)$_2$OMe).

The fluorescent monomer having structure (III) can be 5-allyloxy-4'-carboxy-1,8-naphthoylene-1',2'-benzimidazole ($R^3$=—$CO_2$H and $R^4$=—O$CH_2$CH=$CH_2$). The fluorescent monomer having structure (III) can be 6-vinylbenzyloxy-4'-carboxy-1,8-naphthoylene-1',2'-benzimidazole ($R^3$=—$CO_2$H and $R^4$=4-vinylbenzyloxy).

The synthesis of monomers having structure (I), (II), or (III) is disclosed in U.S. Pat. No. 6,645,428, which is incorporated by reference for its description of these monomers, polymers made from these monomers, and synthesis of such monomers and polymers.

The fluorescent monomers can have structures (IV) or (V):

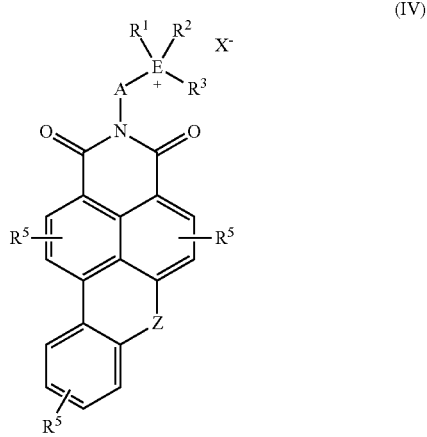

(IV)

-continued (V)

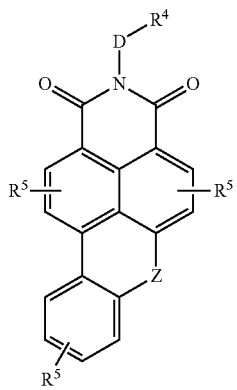

wherein:
A is alkyl, alkoxyalkyl, alkylamidoalkyl, aryl, or is absent; with the proviso that when A is absent, E is nitrogen and E is bonded directly to the imide nitrogen;
E is sulfur or nitrogen with the proviso that when E is sulfur, only one of $R^1$ or $R^2$ is present;
D is alkyl, alkoxyalkyl, alkoxy, alkylamidoalkyl, alkylamino, NH, aryl or is absent;
R is independently hydrogen or alkyl;
$R^1$ and $R^2$ are each independently alkyl;
$R^3$ is allyl, 2-hydroxy-3-allyoxypropyl, vinyl benzyl, 3-methacrylamidopropyl, 3-acrylamidopropyl, 2-acryloxyethyl or 2-methacryloxyethyl;
$R^4$ is allyl, acryl, methacryl, 2-hydroxy-3-allyloxypropyl, vinyl benzyl, 2-acryloxyethyl and 2-methacryloxyethyl;
each $R^5$ is independently hydrogen, halogen, —$NO_2$, —C(O)OH or a salt thereof, —PO(OH)$_2$ or a salt thereof, —$SO_2$(OH) or a salt thereof, or —$SO_2(NR_2)$;
$X^-$ is an anion; and
Z is —$CH_2$—, —C(O)—, —$CR_2$—, —NR—, —$NR_2^+$—, —N(OH)—, —O—, —S—, —S(O)—, or —$SO_2$—.

The fluorescent monomer can be a sulfonated benzoxanthene having structure (IV) or (V), wherein Z=—O— and R=—$SO_3H$.

Monomers having structure (IV) or (V) can be synthesized by reacting a benzoxanthene dicarboxylic anhydride or a sulfonated benzoxanthene dicarboxylic anhydride with a primary amine. The amine can be aliphatic, substituted aliphatic, vinyl, or hydrazine. Materials required for these syntheses are commercially available and can be obtained, for example, from Sigma-Aldrich. Polymerizable moieties can be introduced through substitution on the aromatic ring or during quaternization or imidization.

Preferably, the fluorescent monomer is a sulfonated benzoxanthene having structure (IV), wherein Z=—O—, R=—$SO_3H$, A=—$(CH_2)_3$—, E=N, $R^1$ and $R^2$=Me, and $R^3$=—[$CH_2CH(OH)CH_2OCH_2CH=CH_2$]. This sulfonated benzoxanthene is sulfonated-N-(3-N',N'-dimethylaminopropyl)benzo (k,l) xanthene-3,4-dicarboxylic imide, 2-hydroxy-3-allyloxypropyl quaternary salt. The benzoxanthene can be synthesized according to the method of A. T. Peters and Y. S. S. Behesti in "Benzo[k,l], xanthene-3,4-dicarboximides and benzimidazoxanthenoisoquinolinones -yellow and orange dyes for synthetic-polymer fibres," *Journal of the Society of Dyers and Colourists,* 1989, 105: 29-35, and sulfonated according to the procedure described by H. Troster in U.S. Pat. No. 3,888,863.

The fluorescent monomer can have structure (VI) or (VII):

(VI)

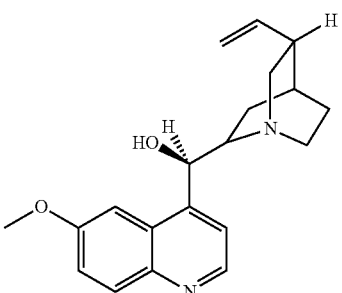

(VII)

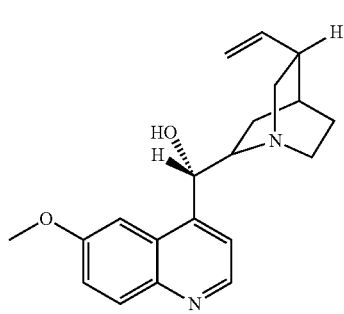

Monomer (VI) is quinine and is commercially available from Sigma-Aldrich Company. Monomer (VII) is quinidine, also commercially available from Sigma-Aldrich. Quinidine, also known as (S)-(6-methoxyquinolin-4-yl)((2R, 4S, 8R)-8-vinylquinuclidin-2-yl)methanol), is a stereoisomer of quinine.

The fluorescent monomer can have structure (VIII) or (IX):

(VIII)

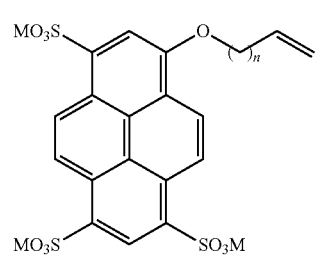

(IX)

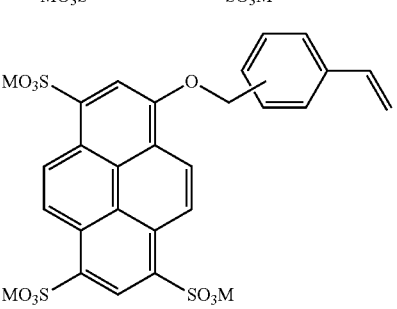

wherein:
M is hydrogen, sodium, potassium, cesium, rubidium, lithium or ammonium; and
n is an integer 1, 2, 3, 4, 6, or 9.

The fluorescent monomer having structure (VIII) can be 8-(allyloxy)-1,3,6-pyrene trisulfonic acid (n=1, M=H).

The fluorescent monomer having structure (IX) can be 8-(3-vinylbenzyloxy)-1,3,6-pyrene trisulfonic acid or 8-(4-vinylbenzyloxy)-1,3,6-pyrene trisulfonic acid (M=H).

These three monomers are prepared by reaction of 8-hydroxypyrene-1,3,6-trisulfonic acid trisodium salt (also called pyranine) with allyl chloride, 3-vinylbenzyl chloride, and 4-vinylbenzyl chloride, respectively. The synthesis of these fluorescent monomers is disclosed in U.S. Pat. No. 6,312,644, which is incorporated by reference for its description of these monomers, polymers made from these monomers, and synthesis of such monomers and polymers.

After preparation and isolation of the fluorescent monomer, polymers containing these fluorescent monomers can be prepared. The polymerization is generally carried out in an aqueous solution through the polymerization of one of the fluorescent monomers with one or more water soluble ethylenically unsaturated monomers. Various polymer initiators can be used in the polymerization including thermal and redox initiators.

Fluorescent Polymers

The compositions of the invention can comprise, and the methods can utilize, a fluorescent polymer derived from direct polymerization of one or more polymerizable fluorescent monomer units with one or more non-fluorescent monomers units, including but not limited to acrylic acid, acrylamide, or 2-acrylamido-2-methylpropane sulfonic acid (a specialty monomer commercially available from Lubrizol Corporation under the trademark name AMPS®).

The fluorescent monomer can be polymerized with one, two, or three additional monomers to give the desired fluorescent polymer.

The compositions of the invention can comprise, and the methods can utilize, a conjugate comprising a fluorescent dye and a non-fluorescent polymer. For example, such a polymer can be formed when a fluorophore is introduced via derivitization of a non-fluorescent polymer. A fluorescent dye can be covalently bonded to the polymer by an appropriate functional group on the polymer chain, for example via an ester, amide, or ether linkage. Here, the fluorescent dyes are pendant to the polymer backbone and not incorporated into the polymer backbone during polymerization.

The fluorescent polymers to be used in the compositions and methods herein are distinguished from fluorescent materials wherein a fluorescent dye is encapsulated by, coated with, or entrapped within a non-fluorescent polymer.

The fluorescent polymers of the invention comprise from about 0.001 to about 10 mole percent of a fluorescent monomer, preferably from about 0.01 to about 0.4 mole percent, and most preferably from about 0.05 to about 0.35 mole percent. For purposes of this patent application, mole percent of all monomers in the fluorescent polymer is calculated based on weight percent of monomers used in the polymerization reaction.

The mole percent of each monomer within the polymer is denoted by subscripts in the general formula given for the polymer. For example, for a polymer derived from fluorescent monomer unit (G) and polymerizable monomer units (Q) and (W) having the formula $G_aQ_jW_t$, subscript a is mole percent of monomer (G), subscript j is mole percent of monomer (Q), and subscript t is mole percent of monomer (W).

The fluorescent polymers were characterized by intrinsic viscosity (IV) and gel permeation chromatography with a differential refractive index detector (GPC/DRI) using standards.

The $M_w$ of the fluorescent polymers suitable for the marking compositions can range from 2 to 2000 kDa, preferably from 3 to 100 kDa, and most preferably from 5 to 50 kDa.

Fluorescent materials (fluorophores) radiate visible light when exposed to ultraviolet light. The fluorescent polymers have a light absorption spectrum in the range of from about 310 to about 400 nm, preferably from about 350 to about 400 nm, and more preferably from about 365 to about 395 nm. The fluorescent polymers have a light emission spectrum in the range of from about 400 to about 750 nm, preferably from about 400 to about 720 nm, more preferably from about 410 to about 700 nm.

The fluorescent polymer can be a random polymer of fluorescent monomer unit (I)-(VII) and polymerizable monomer units (Q), (W), and optionally (S), wherein the polymer has a formula $G_aQ_jW_t$, $G_aQ_vW_fS_c$, or a combination thereof wherein:

G is a fluorescent monomer unit as described herein;

Q is acrylic acid or a salt thereof, methacrylic acid or a salt thereof, maleic acid or a salt thereof, crotonic acid or a salt thereof, maleic anhydride, acrylamide, or acrylamidomethylpropane sulfonic acid or a salt thereof;

S is N-sulfomethacrylamide or N-sulfoethylacrylamide;

W is acrylic acid or a salt thereof, methacrylic acid or a salt thereof, itaconic acid or a salt thereof, maleic acid or a salt thereof, maleic anhydride, crotonic acid or a salt thereof, acrylamide, methacrylamide, vinyl sulfonic acid, styrene sulfonate, N-tert-butylacrylamide, N-isopropylacrylamide, N-butoxymethylacrylamide, N,N-dimethylacrylamide, N,N-diethylacrylamide, dimethylaminoethyl acrylate methyl chloride quaternary salt, dimethylaminoethyl acrylate benzyl chloride quaternary salt, dimethylaminoethyl acrylate methyl sulfate quaternary salt, dimethylaminoethyl methacrylate methyl sulfate quaternary salt, dimethylaminoethyl acrylamide methyl sulfate quaternary salt, dimethylaminopropyl acrylamide methyl sulfate quaternary salt, dimethylaminopropyl methacrylamide methyl sulfate quaternary salt, diallyldimethylammonium chloride, N-vinylformamide, a dimethylaminoethyl methacrylate acid salt, dimethylaminoethyl methacrylate methyl chloride quaternary salt, dimethylaminoethyl methacrylate benzyl chloride quaternary salt, methacrylamidopropyl trimethylammonium chloride, acrylamidopropyl trimethylammonium chloride, N,N'-methylene bisacrylamide, triallylamine, an acid salt of triallylamine, ethylene glycol dimethacrylate, 2-(hydroxymethyl)acrylic acid, 2-hydroxyethyl acrylate, 2-hydroxypropyl acrylate, 2-hydroxypropyl methacrylate, diethylene glycol dimethacrylate, triethylene glycol dimethacrylate, polyethylene glycol dimethacrylate, glycidyl methacrylate, 2-acrylamido2-methylpropane sulfonic acid or a salt thereof, vinyl alcohol, vinyl acetate, or N-vinylpyrrolidone, with the proviso that Q and W cannot both be the same;

a is from about 0.001 to about 10 mole percent;
c is from about 1 to about 40 mole percent;
f is from about 1 to about 97.999 mole percent;
j is from 0 to about 99.999 mole percent;
t is from 0 to about 99.999 mole percent;
v is from 0 to about 97.999 mole percent;
the sum of a, j and t equals 100 mole percent; and
the sum of a, v, f and c equals 100 mole percent.

Preferably, the polymer has the formula $G_aQ_jW_t$, wherein Q is acrylic acid and W is acrylamide; the polymer has the formula $G_aQ_jW_t$, wherein Q is acrylic acid and W is 2-acrylamido-2-methylpropane sulfonic acid; or the polymer has the formula the $G_aQ_vW_cS_c$, wherein Q is acrylic acid, W is acrylamide, and S is N-sulfomethylacrylamide. G can be any one of fluorescent monomer units (I)-(VII as described herein.

A preferred polymer of formula $G_aQ_jW_t$ is derived from polymerization of fluorescent monomer 4-methoxy-N-(3-N',N'-dimethylaminopropyl)naphthalimide 2-hydroxy-3-allyloxypropyl quaternary salt, acrylic acid, and 2-acrylamido-2-methylpropane sulfonic acid, wherein a is 0.2, j is 80.9, and t is 18.9. For purposes of this application, this terpolymer is referred to as "Polymer A".

A second preferred polymer of formula $G_aQ_jW_t$ is derived from polymerization of fluorescent monomer 4-methoxy-N-(3-N',N'-dimethylaminopropyl)naphthalimide 2-hydroxy-3-allyloxypropyl quaternary salt, acrylic acid, and 2-acrylamido-2-methylpropane sulfonic acid, wherein a is 0.2, j is 96.1, and t is 3.7. For purposes of this application, this terpolymer is referred to as "Polymer B".

The fluorescent polymer can be a random polymer of fluorescent monomer unit (VIII) or (XIX) and polymerizable monomer units (B), (C), and (D), wherein the polymer has a formula $G_xB_y$, $G_xB_jC_k$, $G_xB_mD_q$, $G_xB_rC_sD_t$, or a combination thereof wherein:

B is an acrylic acid or a salt thereof, methacrylic acid or a salt thereof, maleic acid or a salt thereof, maleic anhydride, acrylamide, crotonic acid or a salt thereof, or a combination thereof;

C is methacrylic acid or a salt thereof, maleic acid or a salt thereof, maleic anhydride, crotonic acid or a salt thereof, itaconic acid or a salt thereof, acrylamide, methacrylamide, 2-acrylamido-2-methylpropanesulfonic acid or a salt thereof, polyethylene glycol monomethacrylate, vinyl phosphonic acid or a salt thereof, styrene sulfonic acid or a salt thereof, vinyl sulfonic acid or a salt thereof, 3-allyloxy-2-hydroxypropane sulfonic acid or a salt thereof, N-alkyl (meth)acrylamide, t-butyl (meth)acrylate, N-alkyl (meth)acrylate, N-alkanol-N-alkyl(meth)acrylate, vinyl acetate, 2-hydroxy N-alkyl(meth)acrylate, alkyl vinyl ether, alkoxyethyl acrylate, N-alkanol (meth)acrylamide, N,N-dialkyl(meth)acrylamide, 1-vinyl-2-pyrrolidinone, or a combination thereof;

D is sulfomethylacrylamide or sulfoethylacrylamide;
G is fluorescent monomer unit as described herein;
j is from about 1 to about 98 mol %;
k is from about 1.999 to about 98 mol %;
m is from about 1 to about 95 mol %;
q is from about 4.999 to about 40 mol %;
r is from about 1 to about 89.999 mol %;
s is from about 1 to about 89.999 mol %;
t is from about 5 to about 40 mol %;
x is from about 0.001 to about 1 mol %;
y is from about 99.000 to about 99.999 mol %;
the sum of x and y equals 100 mol %;
the sum of x, j and k equals 100 mol %;
the sum of x, m and q equals 100 mol %; and
the sum of x, r, s and t equals 100 mol %.

Preferably, the polymer has the formula $G_xB_y$, wherein B is acrylic acid or a salt thereof; the polymer has the formula $G_xB_jC_k$ wherein B is acrylic acid or a salt thereof, and C is acrylamide; the polymer has the formula $G_xB_jD_q$ wherein B is acrylic acid or a salt thereof, and D is sulfomethylacrylamide; or the polymer has the formula $G_xB_rC_sD_t$ wherein B is acrylic acid or a salt thereof, C is acrylamide, and D is sulfomethylacrylamide. For these polymers, the fluorescent monomer unit (G) has structure (VIII) or (XIX).

Synthesis of Fluorescent Polymers

The fluorescent polymers can be synthesized by following the procedure for conventional free radical polymerization in an aqueous medium. They can be made, for example, by (i) emulsion polymerization; (ii) dispersion polymerization, or (iii) solution polymerization. For those polymers containing a sulfomethylated or sulfoethylated acrylamide, the polymers are first created with an acrylamide moiety, and then the acrylamide groups are sulfomethylated using a suitable reagent such as formaldehyde and sodium metabisulfite.

The preparation of high molecular weight polymers via water-in-oil emulsion polymerization has been described in U.S. Pat. Nos. 2,982,749, 3,284,393, and 3,734,873; "Mechanism, Kinetics and Modelling of the Inverse-Microsuspension Homopolymerization of Acrylamide," by Hunkeler, D., Hamielec, A. and Baade W., *Polymer* (1989), 30(91): 127-142; and "Mechanism, Kinetics and Modelling of Inverse-Microsuspension Polymerization: 2. Copolymerization of Acrylamide with Quaternary Ammonium Cationic Monomers," by D. Hunkeler and A. E. Hamielec; *Polymer* (1991), 32(14): 2626-2640.

A general procedure for the synthesis of water-in-oil emulsion polymers is provided to illustrate the preparation of the fluorescent polymers. The types and quantities of specific components in the polymerization process (e.g., monomers, initiators, and chain transfer agents) will vary depending upon the type of polymer (cationic, anionic, nonionic) that is being synthesized.

An aqueous phase is prepared by mixing together in water one or more water soluble monomers and optional polymerization additives such as inorganic salts, chelating agents, pH buffers, chain transfer agents, and branching or cross-linking agents. In order to synthesize the fluorescent polymer, a polymerizable fluorescent monomer is included in the aqueous phase in the desired amount.

An organic phase is prepared by mixing together an inert hydrocarbon liquid with one or more oil soluble surfactants. The surfactant mixture should have a low hydrophilic-lipophilic balance (HLB) number, to ensure the formation of an oil continuous emulsion. Appropriate surfactants for water-in-oil emulsion polymerizations which are commercially available are compiled in the North American Edition of McCutcheon's *Emulsifiers & Detergents*. The oil phase can be heated to ensure the formation of a homogeneous oil solution.

The oil phase is charged into a reactor equipped with a mixer, a thermocouple, a nitrogen purge tube, and a condenser. Adding the aqueous phase to the reactor containing the oil phase with vigorous stirring forms an emulsion. The resulting emulsion is heated to the desired temperature, purged with nitrogen, and a free-radical initiator is added. The reaction mixture is stirred for several hours under a nitrogen atmosphere at the desired temperature. Upon completion of the reaction, the water-in-oil emulsion polymer is cooled to room temperature, where any desired post-polymerization additives, such as antioxidants, or a high HLB surfactant (as described in U.S. Pat. No. 3,734,873) can be added.

The resulting emulsion polymer is a free-flowing liquid. An aqueous solution of the water-in-oil emulsion polymer can be generated by adding a desired amount of the emulsion polymer to water with vigorous mixing in the presence of a high HLB surfactant (as described in U.S. Pat. No. 3,734,873).

The preparation of dispersion polymers has been described in U.S. Pat. Nos. 4,929,655, 5,006,590, 5,597,858, and 5,597,859, and European Patent Nos. 0630909 and 0657478.

A general procedure for the synthesis of dispersion polymers is provided to illustrate the preparation of the fluorescent polymers. The types and quantities of specific components in the polymerization process (e.g., salts and stabilizer polymers) will vary depending upon the type of polymer (cationic, anionic, nonionic) that is being synthesized.

An aqueous solution containing one or more inorganic salts, one or more water-soluble monomers, and polymerization additives such as chelating agents, pH buffers, chain transfer agents, branching or cross-linking agents, and a water-soluble stabilizer polymer is charged into a reactor equipped with a mixer, a thermocouple, a nitrogen purge tube, and a condenser. The monomer solution is mixed vigorously, heated to the desired temperature, and then a water-soluble initiator is added. The solution is purged with nitrogen while maintaining the temperature and mixing for several hours. After this time, the solution is cooled to room temperature, and post-polymerization additives are optionally charged into the reactor. Water continuous dispersions of water-soluble polymers are free flowing liquids with viscosities generally ranging from 100-10,000 cP (measured at low shear rate). In order to synthesize the fluorescent polymers, a polymerizable fluorescent monomer is included in the aqueous solution in the desired amount.

A general procedure for the synthesis of solution polymers is provided to illustrate the preparation of the fluorescent polymers. One suitable process is as follows. One or more monomers are added to a reaction vessel followed by neutralization with a suitable base. The fluorescent monomer can be added to this monomer solution after neutralization or alternatively, to the reaction vessel. A determined amount of water is then added to the reaction vessel, which is then heated and purged with nitrogen. Polymerization catalysts can be added to the reaction vessel initially or fed into it during the course of the reaction. Water soluble polymerization initiators such as azo or redox initiators or a combination thereof are added along with the monomer solution to the reaction mixture in separate feeds over the same amount of time, usually two to six hours. The reaction temperature is maintained at about 60-70° C. Additional initiator can be used after addition is complete to reduce residual monomer levels.

Other Components in the Fluorescent Marking Compositions

The compositions can be a water-thin liquid, a thickened liquid, a gel or a solid. If included as a thickened liquid or a gel, the compositions can have a viscosity that allows them to be flowable under pressure (e.g., non-Newtonian fluids). Exemplary viscosities include from about 10 to about 6,000 cps, preferably from about 20 to about 200 cps when measured with a Brookfield LVT viscometer at 25° C. with a #1 spindle at 60 rpm.

The compositions include a thickener. The thickener provides a means to reduce inadvertent smearing of the product before cleaning and as a means of modifying the viscosity of the product for application. Exemplary thickeners include, but are not limited to xanthan gum, guar gum, modified guar, a polysaccharide, pullulan, an alginate, a modified starch, hydroxypropyl cellulose, hydroxypropyl methyl cellulose, carboxymethyl cellulose, hydroxyethyl cellulose, hydrophobically modified hydroxyethyl cellulose, hydrophobically modified hydroxypropyl cellulose, a polyacrylate, a vinyl acetate/alcohol copolymer, casein, a urethane copolymer, dimethicone PEG-8 polyacrylate, poly(DL-lactic-co-glycolic acid), a polyethylene glycol, a polypropylene glycol, pectin, or a combination thereof. Preferably, the thickener is a cellulosic polymer such as hydroxyethyl cellulose.

The thickener can be present in the composition in an amount from about 0.01 to about 2 wt. %, from about 0.05 to about 1wt. %, and from about 0.1 to about 0.5 wt. %.

The composition optionally includes a surfactant to assist the composition in depositing on a surface as a layer rather than beading up on the surface. The surfactant can be a nonionic surfactant, an anionic surfactant, a cationic surfactant, an amphoteric surfactant, a silicone surfactant, or a combination thereof.

Exemplary nonionic surfactants include, but are not limited to a linear alkyl alkoxylate, a polyalkylene oxide, an alkylphenol alkoxylate, a branched alcohol alkoxylate, a secondary alcohol alkoxylate, a castor oil alkoxylate, an alkylamine alkoxylate, a fatty acid alkoxylate, a sorbitol oleate alkoxylate, a fatty alkanolamide, an alkyldialkanolamide, a polyalkylene glycol alkylamide, a gemini surfactant containing aromatic or aliphatic hydrophobic groups and polyether hydrophilic groups, or a combination thereof.

Exemplary anionic surfactants include, but are not limited to a C6-C18 fatty acid carboxylate, an alkyl sulfonate, an alkyl sulfate, an alkyl phosphonate, an alkyl phosphate monoester, an alkyl phosphate diester, an alkyl sulfosuccinate, an acyl lactylate, an amino acid bases surfactant (e.g., glycinate, glutamate, alaninate, sarcosinate), a linear alkyl benzene sulfonate, an alkyl aryl sulfonate, an arylalkyl sulfonate alkyl polyglucoside, an alkyl ether carboxylate, and sulfated castor oil, or a combination thereof.

Exemplary cationic surfactants include, but are not limited to, a quaternized sugar-derived surfactant, a quaternized polysaccharide, an alkyl polysaccharide, an alkoxylated amine, an alkoxylated ether amine, cetrimonium bromide, cetrimonium chloride, dioctadecyldimethylammonium chloride, didecyldimethylammonium chloride, trimethylhexadecyl ammonium chloride, benzethonium chloride, a benzalkonium chloride, Bronidox® (i.e., 5-bromo-5-nitro-1,3-dioxane), Glucquat 125® (e.g., lauryl methyl gluceth-10 hydroxypropyl dimonium chloride), or a combination thereof.

Exemplary amphoteric surfactants include, but are not limited to an alkyl amine oxide, an N-alkylamino propionic acid, an N-alkyl-β-imino dipropionic acid, an imidazoline carboxylate, an alkyl betaine, an alkyl amido amine, an alkyl amido betaine, an alkyl sultaine, an alkyl amphodiacetate, an alkyl amphoacetate, an alkyl sulfobetaine, a polymeric sulfobetaine, an amphohydroxypropylsulfonate, a phosphatidylcholine, a phosphatidylethanolamine, a phosphatidylserine, a sphingomyelin, an alkyl amidopropyl phosphatidyl PG-dimonium chloride, or a combination thereof, wherein the alkyl group in the amphoteric surfactant has a carbon length from $C_6$ to $C_{22}$. Preferred amphoteric surfactants include β-alanine N-(2-carboxyethyl)-N-(2-ethylhexyl)-, monosodium salt (commercially available as Tomamine® Amphoteric 400 from Air Products) and disodium caprylo-amphodipropionate (commercially available as Mackam® 2CYSF from Rhodia).

Exemplary silicone surfactants include, but are not limited to, a polydimethylsiloxane polyether, a polydimethylsiloxane copolyether, a polydimethylsiloxane amine, a polydimethylsiloxane phosphate, a polydimethylsiloxane polyether carboxylate, a polydimethylsiloxane quaternary amine, a trisiloxane surfactant, or a combination thereof When the surfactant is present, the surfactant can be present in the composition in an amount from about 0.01 to about 10 wt. %, from about 0.1 to about 7 wt. %, and from about 0.2 to about 5 wt. %.

The compositions include a solvent to assist with solubility and shorten the drying time of the composition on a surface. Exemplary solvents include, but are not limited to, water, methanol, ethanol, n-propanol, isopropanol, n-butanol, 2-butanol, isobutanol, n-pentanol, amyl alcohol, 4-methyl-2-pentanol, 2-phenylethanol, n-hexanol, 2-ethylhexanol, benzyl alcohol, ethylene glycol, ethylene glycol phenyl ether, ethylene glycol mono-n-butyl ether acetate, propylene glycol, propylene glycol mono and dialkyl ethers, propylene glycol phenyl ether, propylene glycol diacetate, dipropylene glycol, dipropylene glycol mono and dialkyl ethers, tripropylene glycol mono and dialkyl ethers, 1,3-propanediol, 2-methyl-1,2-butanediol, 3-methyl-1,2-butanediol, glycerol, methyl formate, ethyl formate, n-propyl formate, isopropyl formate, n-butyl formate, methyl acetate, n-propyl acetate, isopropyl acetate, isobutyl acetate, methyl lactate, ethyl lactate, propyl lactate, dimethylformamide, n-propyl propionate, n-butyl propionate, n-pentyl propionate, amyl acetate, methyl ethyl ketone, methyl isobutyl ketone, diisobutyl ketone, ethylamine, ethanolamine, diethanolamine, formic acid, acetic acid, propanoic acid, butanoic acid, acetone, acetonitrile, acetaldehyde, dimethyl sulfoxide, tetrahydrofuran, or a mixture thereof.

Preferably, the solvent comprises water. The water can be from any source, including deionized water, tap water, softened water, and combinations thereof. The amount of water in the composition ranges from about 40 to about 99 wt. %, preferably from about 60 to about 95 wt. %, and more preferably from about 70 to about 90 wt. %.

The solvent can comprise water and an organic solvent. The total amount of solvent including water and at least one organic solvent ranges from about 60 to 99 wt. %, preferably from about 70 to about 95 wt. %, and more preferably from about 75 to about 90 wt. %.

The compositions can further comprise a preservative, a pH adjusting agent, or a combination thereof.

The compositions can optionally include a preservative to prevent microorganisms from growing in the composition. Exemplary preservatives include, but are not limited to a phenoxyalkanol, a benzoate salt, an alkylchloroisothiazolinone, an alkylisothiazolinone, a benzoic acid salt, a sorbate salt, an alkyl paraban, a glycerin, a glycol, a urea, a hydantoin, a benzalkonium salt, or a combination thereof.

When the preservative is present, the preservative can be present in the composition in an amount from 0.01 to about 5 wt. %, from about 0.01 to about 2.5 wt. %, and from about 0.01 to about 1 wt. %.

The pH of the composition can be adjusted using a suitable acidic or basic pH adjusting agents. Exemplary pH adjusting agents include, but are not limited to: a hydroxy acid (e.g., acid, sodium salt, and potassium salt forms of citric acid, gluconic acid, glycolic acid, lactic acid, succinic acid, acetic acid, formic acid, ascorbic acid); an amino acid (e.g., acid and salt forms of glycine, histidine, isoleucine, lysine, methionine, glutamine, cysteine, asparagine, arginine, alanine, glutamic acid, aspartic acid); phosphoric acid (e.g., acid, sodium salt, and potassium salt forms); potassium hydroxide, potassium carbonate, potassium bicarbonate, sodium hydroxide, sodium carbonate, sodium bicarbonate, ammonium hydroxide, a primary amine (e.g., ethanolamine, aminomethyl propanol, tris(hydroxymethyl) aminomethane), a secondary amine (e.g., diisopropylamine), a tertiary amine (e.g., triethylamine, triisopropylamine, nitrilotriacetic acid), a diamine or salt thereof (ethylenediamine, ethylenediaminetetraacetic acid, N-(2-hydroxyethyl) ethylenediamine-N,N',N'-triacetic acid, tetrahydroxypropyl ethylenediamine), a triamine or salt thereof (e.g., diethylene triamine pentaacetic acid) or a combination thereof.

To prepare the marking compositions, the fluorescent polymer, solvent, thickener, and optional additives such as a surfactant, a preservative, and a pH adjusting agent are combined at ambient temperature and mixed thoroughly. When preparing marking compositions using modified cellulose ether thickeners, it is advantageous to active the cellulose ethers prior to the addition of the fluorescent polymer. For ready-to-use compositions, the desired amount of solvent will be added. For ready-to-use compositions, the desired amount of solvent will be added. For concentrated solutions, typically a reduced volume of solvent is added.

Examples of commercial sources of suitable components are as follows:

TABLE 1

| Composition | Description | Trade Name | Supplier |
| --- | --- | --- | --- |
| Thickener | Hydroxypropylmethylcellulose | Methocel® 40-100 | Dow Chemical |
| | Hydroxyethylcellulose | Natrosol® 250 H4BR | Ashland |
| | Xanthum gum clear | Keltrol® CG-T | CP Kelco |
| | Polysaccharide polymer consisting of maltotriose units | Pullulan® | Hayashibara Biochemical |
| Surfactant | β-alanine, N-(2-carboxyethyl)-N-(2-ethylhexyl)-, monosodium salt | Tomamine® Amphoteric 400 | Air Products |
| | β-alanine, N-(2-carboxyethyl)-N-[3-(octyloxy)propyl]-, monosodium salt | Tomamine® Amphoteric 12 | Air Products |
| | Alkyloxypropylamine | Tomamine® AO-405 | Air Products |
| | Linear C9/C10/C11 ethoxylated alcohol (8 moles EO) | Tomadol(12® 91-8 | Air Products |
| | Proprietery blend of C9-11 ethoxylated alcohols and C10-16 ethoxylated alcohols | Tomadol® 901 | Air Products |
| | Branched C10 ethoxylated Guerbet alcohol (8 moles EO) | Lutensol XP-80 | BASF |

TABLE 1-continued

| Composition | Description | Trade Name | Supplier |
|---|---|---|---|
| | N,N-Dimethyldodecan-1-amine oxide | Barlox ® 12i | Lonza |
| | Disodium capryloamphodipropionate | Mackam ® 2CYSF | Rhodia |
| | Diethylhexyl sodium sulfosuccinate | Mackanate ® DOS-75 | Rhodia |
| Solvent | Water | Water | |
| | 2-Propanol | Isopropyl alcohol | Brenntag |
| | Propylene glycol n-propyl ether | Dowanol ® PnP | Dow Chemical |
| | Dipropylene glycol n-propyl ether | Dowanol ® DPnP | Dow Chemical |
| | Propylene glycol methyl ether | Dowanol ® PM | Dow Chemical |
| Preservative | 1,2-Benzisothiazolin-3-one | Proxel ® GXL | Arch Biocides |
| | Phenoxyethanol | Phenoxetol ® | Clariant |
| | Sodium benzoate | | EMERALD KALAMA CHEMICAL, LLC |
| | Chloro methyl isothiazolinone | Kathon ® CG | Dow Chemical |
| pH Adjusting agent | Sodium hydroxide (50% soln. in water) | | Sigma-Aldrich |
| | Citric acid (50% soln. in water) | | Tri-Chem Industries |

Use of Fluorescent Marking Compositions

Cleaning of patient rooms is an ongoing process in a hospital. Each patient occupying a room can be subject to pathogens left by a prior occupant of the hospital and, in turn, can insert his or her specific pathogens into the room environment. During the patient's hospitalization, pathogens can also be introduced into the room by contact with healthcare providers, staff, and visitors. An aim of room cleaning is to decrease the likelihood of the environmental transmission of infection to an occupant of the room. Some room sites are cleaned daily while others are cleaned following patient occupation. Generally, such cleaning is unsupervised. Correlation of the health of room occupants could provide an indication of the quality of the cleaning, although with significant effort and with significant delay.

Examples discussed below illustrate where monitoring can provide timely assessment as to whether current cleaning activities are consistent with control over nosocomial infections any can have the potential for objectively evaluating cleaning and disinfecting activities in various healthcare settings. A nontoxic composition containing a polymer which fluoresces with exposure to UV light is inconspicuous yet can be readily removed by housekeeping products. Small volumes of the disclosed composition can be confidentially applied to target sites in patient rooms following cleaning and the targets reevaluated following cleaning.

The monitoring method can indicate acceptable cleaning of traditional sites but poor cleaning of other sites which have significant potential for harboring and transmitting microbial pathogens. An integrated program can identify such deficiencies in hospital cleaning and target remediation efforts so as to accelerate reduction in pathogen levels.

For example, a hospital room typically comprises a bed in association with bed rails, bed tray, drape, and drape support. Patient call box and telephone are generally located near the bed and provide communication, where the telephone rests on a table. A chair often is present and provides additional seating. A sink including a faucet, handles, and bedpan flushing device provide a cleansing facility. A toilet containing a sink and handle resides in the patient bathroom. A grab bar provides support for a patient in using the toilet. Entry into the room and bathroom is through doors typically via engagement of a handle or push plate. Room lights can be adjusted by a room light switch monitored on a room light switch plate. Bathroom lights can be adjusted by a bathroom light switch mounted on a bathroom light switch plate. The hospital room can have a television whose operation is controlled by a remote control device. The room can have a work station with a computer, keyboard, and keyboard hand rest.

Target locations for monitoring are those which correspond to areas of a surface and can be chosen based on their classification as "high touch objects" (HTOs). Such targets can include a toilet handle, a toilet seat, a bedpan flushing device, a faucet handle, a doorknob or door handle, a push plate, a grab plate, a toilet area grab bar, a telephone receiver, a call button, a table, a chair seat, a chair arm, a bedrail, a drape, a room light switch, a computer mouse, a keyboard wrist rest, and a soap dispenser.

To the degree possible, suitable locations for the compositions include an area which is easily accessible for cleaning and in close proximity to the portion of the object most frequently contaminated by patients' and health care workers' hands. As a consequence of this separation, the composition placed in these locations is not subject to removal by the actions of the patient during the interval between placement of the composition and the subsequent examination of the location. In addition, proximity of the location to areas subject to patient contact makes probable that cleaning of the composition correlates with cleaning of the patient contact areas. An example is a toilet handle that is separated from, but in the proximity of the area most likely to receive patient contact during use and be contaminated.

The composition can be controllably applied to a location by an applicator or applicator system. The disclosed compositions can be applied with a broad range of applicators, including but not limited to a spray applicator (e.g., with a spray angle of 5° to 60° or 15° to) 30°), a foam pad applicator, a shoe-polish type applicator, a felt tip applicator (similar to a highlighter marker), a brush, a roll, a wipe, or a solid form (e.g. eraser style, solid pen, chalk, etc.). The applicator can be a plastic squeeze bottle or a combination of a squeeze bottle or ampule with a foam pad attached to the end. The disclosed compositions can have a viscosity that allows for other methods of application which were not previously acceptable for currently available formulations, such as dispensing into an individual gel applicator or an applicator pad or felt tipped pad as those found on highlighter markers.

The compositions can be inconspicuous, transparent, semi-transparent, opaque, or semi-opaque, either in the applicator, on a surface, or both. Preferably, the compositions are environmentally stable, nontoxic, rapidly dried, readily wetted by spray disinfectants, liquid disinfectants, or other cleaning agents, and easily removed by light abrasion.

To objectively evaluate cleaning outcomes, the disclosed compositions are applied to surfaces such as, for example, the high touch objects indicated herein, and allowed to dry. Since the dried composition does not occupy a location likely to encounter abrasion from daily activities, its removal can be assumed to be the result of cleaning activities. The dried composition is transparent or semi-transparent and is generally inconspicuous, so that those engaged in cleaning activities are unaware of its location. This allows the cleaning staff to perform their work without bias as to the presence of the fluorescent marking composition on an object.

After cleaning, the high touch objects are inspected with a UV light source to determine if the marks were removed, indicating whether or not the object was thoroughly cleaned. Exemplary UV light sources emit light having a wavelength range of from about 310 to about 400 nm, preferably with a range of from about 350 to about 400 nm, more preferably with a range of from 365 to about395 nm. This wavelength range is selective enough so that, when illuminated with the UV light source, the dried composition is easily visible but surfaces not marked with the composition do not otherwise fluoresce. The UV light source can be, for example, a pen, a wand, or a flashlight. The UV light source is preferably a pen with a radiation cone angle of 5-40°, 10-30°, or 15-20°.

The composition can be a concentrate that is diluted to a desired concentration before use. Alternatively, the composition can be "ready to use" and is provided in a desired applicator at the desired use concentration. The disclosed compositions can be stored in bulk and then divided into dispensers or applicators for use.

The fluorescent marking composition is applied to the high touch objects with a suitable applicator. Exemplary applicators include, but are not limited to, a foam applicator, a spray container, a cotton swab, or a roll-on dispenser.

The fluorescent marking composition is allowed to dry on the surface of the high touch object before cleaning the HTO with a disinfectant. Exemplary disinfectants include, for example, alcohol, quaternary ammonium compounds, chlorine based products, hydrogen peroxide, and phenolics.

The cleaning solution/disinfectant can be used, for example, with a microfiber cloth, a cotton fiber cloth, a disposable woven cloth, or a non-woven cloth.

After cleaning, the lights in the room are dimmed as low as possible, the surface of the HTO is illuminated with UV light, and the presence or absence of a fluorescent mark is made by visual observation.

Mobile applications can be used to help hospitals record and keep track of cleaning outcomes as rooms are inspected. As auditors inspect rooms after cleaning, they identify whether an object has passed or failed from a list of high touch objects within the room. The data can be wirelessly transmitted, aggregated, and analyzed.

Based on the data, reports on cleaning effectiveness can be prepared. Such reports can include, for example, the percentage of high tough objects cleaned, a comparison against baseline data collected before a cleaning program was implemented, and identification of areas for improvement. An example of a data collecting and reporting system is found is U.S. Pat. No. 8,639,527, which is incorporated herein by reference in its entirety.

The fluorescent marking compositions can be used to monitor the cleaning of a high touch surface in a hospital, nursing home, long-term care facility, clinic, doctor's office, and other health care settings. In addition, the compositions could be used more broadly to monitor cleaning/disinfecting processes in other environments. For example, the fluorescent marking compositions are suitable for use in other locations, such as, for example, restaurants, bars, nightclubs, grocery stores, hotels, banks, dental offices, spas, health clubs and fitness centers, locker rooms, day care centers, indoor playgrounds, schools, convention centers, office buildings, public restrooms, movie theaters, places of worship (e.g., churches, temples, synagogues, mosques), public transit (e.g., trains, subways, buses, trams), airplanes, taxicabs, cruise ships, and ferries. Provided the inspection can be conducted in an area that allows for visualization of fluorescence with UV light, the method and compositions of the present invention can be employed in any location or area where verification of cleaning or disinfection of a particular surface or collecting of surfaces is desired.

A kit is also provided which comprises a fluorescent marking composition, a dispenser for dispensing the composition or an applicator for applying the composition to a surface, and optionally a portable ultraviolet light emitting light source The uv light source emits light having a wavelength range of from about 310 to about 400 nm, preferably with a range of from about 350 to about 400 nm, more preferably with a range of from 365 to about 395 nm. For example, the UV light source in the kit can be a 12 LED bulb UV flashlight (e.g., Abco Tech 12 LED UV 375 nm 3 AAA flashlight), that emits light having a wavelength of 375 nm.

As used in this description and the accompanying claims, the following terms shall have the meanings indicated, unless the context otherwise requires:

Fluorescent materials (fluorophores) radiate visible light when exposed to ultraviolet light. Fluorophores absorb photons of energy ($hv_{EX}$) supplied by an external source creating an excited singlet state. After a finite time and partial dissipation of energy, a photon of energy of lower energy and longer wavelength ($hv_{EM}$) is emitted from a relaxed singlet excited state, returning the fluorophore to its ground state. The time interval between absorption of excitation light and emission of re-radiated light is usually less than a millionth of a second. The difference in the excitation and emission wavelengths is called the Stokes shift. The quantum yield is an indicator of the efficiency of the fluorophore (i.e. ratio of emitted photons per absorbed photon) and the extinction coefficient is the amount of light that can be absorbed by a fluorophore. The quantum yield and extinction coefficient are specific for each fluorophore, and multiplied together calculates the brightness of the fluorescent molecule.

Ultraviolet (UV) light is electromagnetic radiation with a wavelength range between 400 nm and 100 nm. This wavelength range is shorter than that of visible light.

Polymers are macromolecular chemical compounds consisting of repeating units, called "monomers" or "monomer units." As used herein, the longest continuous polymeric chain of a polymer is referred to as the "backbone." All other polymer chains are side chains or branches. Polymers derived from polymerization of a single monomer are homopolymers. Polymers derived from polymerization of two monomers are copolymers. Polymers derived from polymerization of three monomers are terpolymers. The polymers in the invention consist of at least two different monomers, and hence the term "polymer" herein refers to copolymers, terpolymers, etc. As used herein, the term "random polymer" refers to a polymer comprising more than one monomer unit wherein the monomers are connected in random order along a polymer chain.

The molecular weight of a polymer is an average weight of the molecules in the mixture of different size molecules that make up the polymer. The two averages most commonly used to characterize a polymer are Number Average Molecular Weight ($M_n$) and Weight Average Molecular Weight ($M_w$). All molecular weights herein are weight average molecular weights ($M_w$) determined by gel permeation chromatography (GPC) using polystyrene sulfonate standard calibration. For detection, both refractive index and fluorescence detectors were used. The columns used were Micra® GPC500+GPC 100. The mobile phase was 70/30 water/acetonitrile containing 0.15 M ammonium formate (to reduce sticking of the small amount of highly aromatic unreacted fluorescent monomer).

Having described the invention in detail, it will be apparent that modifications and variations are possible without departing from the scope of the invention defined in the appended claims.

EXAMPLES

The following non-limiting examples are provided to further illustrate the present invention.

Example 1

Synthesis of fluorescent monomer 4-methoxy-N-(3-N',N'-dimethylaminopropyl)naphthalimide 2-hydroxy-3-allyloxypropyl quaternary salt ("BRT1").

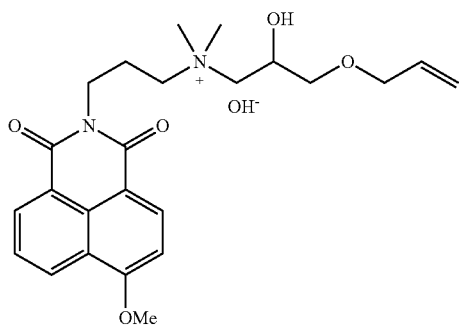

Step One: Synthesis of 4-chloro-N-(3-N',N'-dimethylaminopropyl)-naphthalimide (I)

A 500 mL 3-necked round bottom flask equipped with a mechanical stirrer (½ moon Teflon blade) and water condenser was charged with 4-chloro-1,8-naphthalic anhydride (23.3 g, 0.1 mol), 3-dimethylaminopropylamine (10.37 g, 0.102 mol), and glacial acetic acid (21 mL). The mixture was heated to reflux with stirring for three hours. Upon cooling, deionized water (200 mL) was added, followed by 50% sodium hydroxide solution (32 g, 0.3875 mol). The resulting tan precipitate was collected by filtration, washed with deionized water, and dried under vacuum.

Step Two: Synthesis of 4-methoxy-N-(3-N',N'-dimethylaminopropyl)-naphthalimide (II)

A 250 mL 3-necked round bottom flask equipped with a mechanical stirrer (1/2 moon Teflon blade) and water condenser was charged with the entire quantity of 4-chloro-N-(3-N',N'-dimethylaminopropyl)naphthalimide (I) produced above, sodium methoxide (10.8 g, 0.2 mol) and methanol (25 mL). The contents of the flask were heated to reflux with stirring for five hours. Upon cooling, the excess sodium methoxide was neutralized with 12 M hydrochloric acid until the pH was ca. 10.5. The solvent was stripped and the crude orange/yellow residue was used directly in the next step.

Step Three: Synthesis of 4-methoxy-N-(3-N',N'-dimethylaminopropyl)-naphthalimide 2-hydroxy-3-allyloxypropyl quaternary salt ("BRT1").

A 50 mL round bottom flask was charged with 4-methoxy-N-(3-N',N'-dimethylaminopropyl)naphthalimide (II) (3.0 g, 9.612 mmol), allyl glycidyl ether (1.15 g, 10 mmol), and deionized water (37 mL). The contents of the flask were heated to 60° C. with stirring. The reaction solution became homogeneous after approximately thirty minutes. The reaction was held at temperature for 2.5 hours, and then cooled. $^1$H NMR and $^{13}$C NMR data were consistent with the structure of the expected product.

Example 2

Synthesis of fluorescent monomer 5-allyloxy-4'-carboxy-1,8-naphthoylene-1',2'-benzimidazole

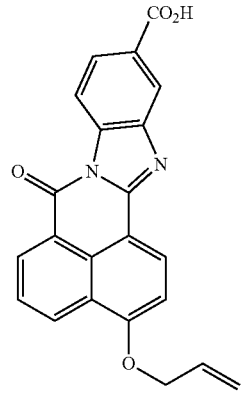 [SMILES: C=CCOc1ccc2c3c1cccc3c(=O)n1c3ccc(C(=O)O)cc3nc21]

Step One: Synthesis of 5-chloro-4'-carboxy-1,8-naphthoylene-1',2'-benzimidazole (I)

A 100 mL round bottom flask was charged with 4-chloro-1,8-naphthalic anhydride (4.65 g, 19.99 mmol), 3,4-diaminobenzoic acid (3.08 g, 20.24 mmol), and glacial acetic acid (50 mL). The mixture was heated at reflux under nitrogen for five hours and then cooled. The solid was collected, washed with isopropanol, and dried under vacuum.

Step Two: Synthesis of 5-allyloxy-4'-carboxy-1,8-naphthoylene-1',2'-benzimidazole A 300 mL Parr reactor was charged with 5-chloro-4'-carboxy-1,8-naphthoylene-1',2'-benzimidazole (I) (0.7 g, 2.01 mmol), allyl alcohol (20 mL, 0.294 mol), and potassium hydroxide (0.23 g, 4.1 mmol). The reactor was purged for 10 minutes, sealed, and then heated at 150° C. for four hours. Upon cooling, the volatiles were stripped and a crude orange solid was obtained.

Example 3

Synthesis of fluorescent monomer 6-vinylbenzyloxy-4'-carboxy-1,8-naphthoylene-1'2'-benzimidazole

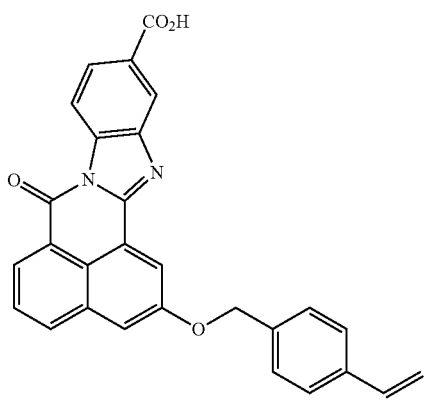 [SMILES: C=Cc1ccc(COc2cc3cccc4c(=O)n5c6ccc(C(=O)O)cc6nc5c(c2)c34)cc1]

Step One: Synthesis of 6-hydroxy-4'-carboxy-1,8-naphthoylene-1',2'-benzimidazole (I)

A 100 mL round bottom flask was charged with 3-hydroxy-1,8-naphthalic anhydride (4.29 g, 20.04 mmol), 3,4-diaminobenzoic acid (3.04 g, 19.97 mmol), and glacial acetic acid (50 mL). The mixture was heated at reflux under nitrogen for five hours and then cooled. The solid was collected, washed with isopropanol, and dried under vacuum.

Step Two: Synthesis of 6-vinylbenzyloxy-4'-carboxy-1,8-naphthoylene-1'2'-benzimidazole.

A 100 mL round bottom flask was charged with 6-hydroxy-4'-carboxy-1,8-naphthoylene-1',2'-benzimidazole (I) (1.66 g, 4.5 mmol), vinyl benzyl chloride (0.92 g, 6.05 mmol), and potassium carbonate (2.38 g, 10 mmol). The mixture was heated at reflux in acetone for eight hours and then cooled. The mixture was then poured into water, acidified, and the orange solid was collected.

Example 4

Synthesis of fluorescent monomer 8-(allyloxy)-1,3,6-pyrene trisulfonic acid, trisodium salt

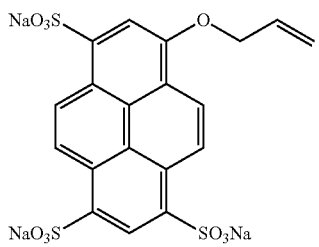

A 100 mL flask was charged with 8-hydroxy-1,3,6-pyrene trisulfonic acid (2.62 g, 5.0 mmol) and dry dimethyl sulfoxide (25 mL) under a nitrogen atmosphere. A 50% aqueous sodium hydroxide solution (6.0 mmol) was added, and the reaction mixture was stirred for twenty minutes at room temperature. In one portion, allyl chloride (0.46 g, 6.0 mmol) was added. Stirring was continued at room temperature for an additional six hours. The reaction mixture was filtered to remove sodium chloride, then dimethyl sulfoxide solvent was distilled off under vacuum (1.0 torr) at 40° C. The residue was stirred in 100 mL acetone. Insoluble product was filtered, collected, and dried to give 8-(allyloxy)-1,3,6-pyrene trisulfonic acid, trisodium salt as a yellow solid in over 90% yield.

Example 5

Synthesis of fluorescent polymer A [0.2 mole % 4-methoxy-N-(3-N',N'-dimethylaminopropyl)-naphthalimide 2-hydroxy-3-allyloxypropyl quaternary salt/80.9 mole % acrylic acid/18.9 mole % 2-acrylamido-2-methylpropane sulfonic acid]

A reactor was charged with deionized water (44.8 g) and 4-methoxy-N-(3-N',N'-dimethylaminopropyl)naphthalimide 2-hydroxy-3-allyloxypropyl quaternary salt (0.38 g) and heated to 65° C. with stirring at 750 rpm. At temperature, initiator solution one (0.55 g sodium persulfate in 3.68 g of deionized water) and initiator solution two (1.6 g sodium metabisulfite in 2.4 g of deionized water) were added separately at a constant flow rate over a period of 3.25 hours. Five minutes after initiator feed had started, 54.0 g of acrylic acid and 36.0 g of 50% 2-acrylamido-2-methylpropane sulfonic acid sodium salt solution were added separately at a constant flow rate over a period of three hours. After thirty minutes, 50% aqueous sodium hydroxide (0.88 g) was added. After monomer and initiator feeding was complete, the reaction was held at temperature for an additional thirty minutes.

Example 6

Synthesis of fluorescent polymer B [0.2 mole % 4-methoxy-N-(3-N',N'-dimethylaminopropyl)-naphthalimide 2-hydroxy-3-allyloxypropyl quaternary salt/96.1 mole % acrylic acid/3.7 mole % 2-acrylamido-2-methylpropane sulfonic acid]

A reactor was charged with deionized water (245.1 g) and 4-methoxy-N-(3-N',N'-dimethylaminopropyl)naphthalimide 2-hydroxy-3-allyloxypropyl quaternary salt (0.38g) and heated to 65° C. with stirring at 750 rpm. At temperature, initiator solution one (1.1 g sodium persulfate in 3.3 g of deionized water) and initiator solution two (3.7 g sodium metabisulfite in 6.1 g of deionized water) were added separately at a constant flow rate over a period of 3.25 hours. Five minutes after initiator feed had started, 82.2g of acrylic acid and 9.2g of 50% 2-acrylamido-2-methylpropane sulfonic acid sodium salt solution were added separately at a constant flow rate over a period of three hours. After thirty minutes, 50% aqueous sodium hydroxide (1.33 g) was added. After monomer and initiator feeding was complete, the reaction was held at temperature for an additional 30 minutes.

Example 7

Synthesis of fluorescent polymer [0.04 mole % 5-allyloxy-4'-carboxy-1,8-naphthoylene-1',2'-benzimidazole/49.98 mole % acrylic acid/49.98 mole % acrylamide]

A reactor was charged with deionized water (125 g) and 5-allyloxy-4'-carboxy-1,8-naphthoylene-1',2'-benzimidazole (0.474 g, 1.16 mmol) and heated to 65° C. with stirring at 750 rpm. At temperature, initiator solution one (3.50 g ammonium persulfate in 19.59 g of deionized water) and initiator solution two (10.48 g sodium metabisulfite in 30.30 g of deionized water) were added separately at a constant flow rate over a period of 3.25 hours. Five minutes after initiator feed had started, a monomer solution consisting of deionized water (13.57 g), acrylic acid (95.43 g, 1.33 mol), 48.7% acrylamide (193.23 g, 1.33 mol), and 50% aqueous sodium hydroxide (42.3 g, 0.529 mol) was added separately at a constant flow rate over a period of three hours. After monomer and initiator feeding was complete, the reaction was held at temperature for an additional thirty minutes. The product had a weight average molecular weight of approximately 11.6 kDa.

Example 8

Synthesis of fluorescent polymer [0.04 mole % 6-vinylbenzyloxy-4'-carboxy-1,8-naphthoylene-1',2'-benzimidazole/49.98 mole % acrylic acid/49.98 mole % acrylamide]

A 5 neck, 1000 mL resin flask equipped with a mechanical stirrer, side baffles, reflux condenser, and nitrogen purge was charged with deionized water (133.96 g) and heated to 65° C. with stirring (800 rpm). At temperature, initiator solution one (2.56 g ammonium persulfate in 30 g of deionized water), initiator solution two (7.74 g sodium metabisulfite in 30 g of deionized water), and a monomer solution consisting of acrylic acid (88.12 g, 1.22 mole), 49.6% acrylamide (177.56 g, 1.22 mole), 50% aqueous sodium hydroxide (36.4 g, 0.455 mole), and 6-vinylbenzyloxy-4'-carboxy-1,8-naphthoylene-1',2'-benzimidazole (0.42 g, 0.943 mmol) were added separately at a constant flow rate over a period of two hours. After monomer and initiator feeding was complete, the reaction was held at temperature for an additional one hour. The product had a weight average molecular weight of approximately 15 kDa.

Example 9

Synthesis of fluorescent polymer [0.04 mole % 4-methoxy-N-(3-N',N'-dimethylaminopropyl)naphthalimide 2-hydroxy-3-allyloxypropyl quaternary salt/49.98 mole % acrylic acid/49.98 mole % acrylamide]

A reactor was charged with deionized water (125 g) and 4-methoxy-N-(3-N',N'-dimethylaminopropyl)naphthalimide 2-hydroxy-3-allyloxypropyl quaternary salt (0.95g) and heated to 65° C. with stirring at 750 rpm. At temperature, initiator solution one (3.50 g ammonium persulfate in 19.59 g of deionized water) and initiator solution two (10.48 g sodium metabisulfite in 30.30 g of deionized water) were added separately at a constant flow rate over a period of 3.25 hours. Five minutes after initiator feed had started, a monomer solution consisting of deionized water (13.57 g), acrylic acid (95.43 g, 1.33 mole), 48.7% acrylamide (193.23 g, 1.33 mole), and 50% aqueous sodium hydroxide (42.3 g, 0.529 mole) was added separately at a constant flow rate over a period of three hours. After monomer and initiator feeding was complete, the reaction was held at temperature for an additional 30 minutes. The product had a weight average molecular weight of approximately 11.6 kDa.

Example 10

Synthesis of fluorescent polymer [0.13 mole % 8-(allyloxy)-1,3,6-pyrene trisulfonic acid /49.935 mole % acrylic acid/49.935 mole % acrylamide]

A 1.0 L reactor equipped with side baffles and nitrogen purge was charged with distilled water (130.34 g, 7.24 mmol) and heated to 60° C. with vigorous stirring at 800 rpm. While the temperature was maintained at 60° C., a monomer solution (adjusted to pH 5 with 50% aqueous NaOH) consisting of acrylic acid (88.12 g, 1.22 mole), 49.6% acrylamide (175.16 g, 1.22 mol) and 1 wt. % 8-(allyloxy)-1,3,6-pyrene trisulfonic acid; initiator solution one (2.56 g ammonium persulfate in 30 g of deionized water); and initiator solution two (7.74 g sodium metabisulfite in 28.0 g of deionized water) were added separately at constant flow rates over a period of two hours. The reaction was then maintained at 60° C. for an additional one hour period.

Example 11

Fluorescent Marking Compositions

A series of 148 compositions were formulated based on the components listed in Table 1. For each solution, its clarity and the presence/absence of precipitate was noted. The broadest range tested and a preferred amount for each component is given in Table 2.

TABLE 2

| Component | Range tested (wt. %) | Preferred amount (wt. %) |
|---|---|---|
| Water | 47 to 97.6 | 47 to 56 |
| organic solvent | 0 to 5.5 | 0 |
| fluorescent polymer:[1] | | |
| 42 wt. % solution of fluorescent Polymer A | 24.49 to 25.06 | 25 |
| 28 wt. % solution of fluorescent Polymer A | 42 | 42 |
| Surfactant | 0 to 8.5 | 2 to 6 |
| Preservative | 0 to 1.2 | 0.5 to 0.7 |
| Thickener | 0 to 3 | 0.2 |
| pH adjusting agent | 0 to 0.69 | 0.1 to 0.69 |

[1]The fluorescent polymer was either a 42 wt. % or a 28 wt. % solution of Polymer A.

Optimization of the components provided a representative formulation for the fluorescent marking composition, as shown in Table 3.

TABLE 3

| Component | Description | % w/w |
|---|---|---|
| Solvent | Purified water, U.S.P. | 52.925 |
| fluorescent polymer | 28 wt. % solution of Polymer A | 42.000 |
| surfactant 1 | Tomamine ® Amphoteric 400 | 4.000 |
| surfactant 2 | Mackam ® 2CYSF | 0.050 |
| preservative 1 | Phenoxyethanol | 0.500 |
| preservative 2 | Sodium benzoate | 0.200 |
| Thickener | Hydroxyethylcellulose | 0.175 |
| pH adjusting agent | NaOH, 50% solution | 0.150 |

The marking compositions were then utilized in two different field trials on various high touch objects to determine if they left a ghost mark or were completely removable. In a first field trial, eight formulations were tested at a hospital on six HTOs, including a table, a bed rail, a chair arm, a toilet seat, a keyboard wrist rest, and a bathroom rail.

Formulations 1 and 2 comprised fluorescent monomer 4-methoxy-N-(3-N',N'-dimethylaminopropyl)naphthalimide, allyl chloride quaternary salt but no polymer. Formulations 3 and 4 comprised fluorescent Polymer A. Formulations 5 and 6 comprised fluorescent Polymer B. Formulation 7 comprised a non-fluorescent polymer C comprised of acrylic acid and 2-acrylamido-2-methylpropane sulfonic acid. Formulation 8 comprised non-fluorescent polymer C and fluorescent monomer 4-methoxy-N-(3-N',N'-dimethylaminopropyl)naphthalimide, allyl chloride quaternary salt. The composition of Test Formulations 1-8 is shown in Table 4.

TABLE 4

Composition of Test Formulations 1-8

| Formulation Number | Water | Hydroxyethyl cellulose | NaOH 50% soln. | Monomer or Polymer | Tomamine ® Amphoteric 400 |
|---|---|---|---|---|---|
| 1 | 99.40 | — | — | 0.60; Monomer[1] | — |
| 2 | 93.15 | 0.20 | 0.05 | 0.60; Monomer[1] | 6.00 |
| 3 | 58.00 | — | — | 42.00; Polymer A solution[2] | — |
| 4 | 51.75 | 0.20 | 0.05 | 42.00; Polymer A solution[2] | 6.00 |
| 5 | 75.00 | — | — | 25.00; Polymer B solution[3] | — |
| 6 | 68.75 | 0.20 | 0.05 | 25.00; Polymer B solution[3] | 6.00 |
| 7 | 75.00 | — | — | 25.00; Polymer C solution[4] | — |
| 8 | 68.40 | 0.20 | 0.05 | 0.50; Monomer[1] 24.88; Polymer C solution[4] | 5.97 |

[1]Fluorescent monomer 4-methoxy-N-(3-N',N'-dimethylaminopropyl)naphthalimide, allyl chloride quaternary salt ("BRT1");
[2]28 wt. % solution of Polymer A [BRT1:AA:AMPS (0.2:80.9:18.9)];
[3]47 wt. % solution of Polymer B [BRT1:AA:AMPS (0.15:96.1:3.74)];
[4]51 wt. % solution of Polymer C [AA:AMPS (81:19)].

In the first field trial, approximately 2 mL of each formulation was filled into an applicator ampoule and sealed. In the hospital, the ampoule end was opened to allow product to flow through the foam applicator head. One spot was made on each HTO by depressing the applicator firmly on the surface. All surfaces were pre-labeled to ensure that correct readings were made.

Upon treatment of the sites, the spots were allowed to dry for 5 to 10 minutes. Once dry, the spots were evaluated using a UV light source (12 LED bulb UV flash light) with a 375 nm output. After verifying which spots fluoresced, a microfiber cloth saturated with OxyCide® disinfectant cleaner was wiped across the surface of the HTO. (OxyCide® is a hydrogen peroxide/peracetic acid based antimicrobial composition commercially available from Ecolab Inc.). The cleaned surfaces were allowed to dry, and then the sites were evaluated using UV light (375 nm) for ghost marks on the surface. As expected, all formulations displayed fluorescence except for formulation 7, which did not have any fluorescent components (either monomer or polymer). Formulations 3, 4, 5, and 6 fluoresced, were completely removed by cleaning, and did not leave a ghost mark on any of the HTOs. Formulations 1 and 2, comprising only the fluorescent monomer, fluoresced but left ghost marks on two of the six HTOs. Thus, fluorescent Polymers A and B overcame the problem of ghost marks observed with known fluorescent marking compositions. The results of field trial 1 are shown in Table 5, wherein N indicates no ghost marks were observed and G indicates that ghost marks were observed.

TABLE 5

Results of Field Trial 1

| Formulation Number | High Touch Object | | | | | |
|---|---|---|---|---|---|---|
| | table | bed rail | chair arm | toilet seat | keyboard wrist rest | bathroom rail |
| 1 | N | G | G | N | N | N |
| 2 | N | G | G | N | N | N |
| 3 | N | N | N | N | N | N |
| 4 | N | N | N | N | N | N |

TABLE 5-continued

Results of Field Trial 1

| Formulation Number | High Touch Object | | | | | |
|---|---|---|---|---|---|---|
| | table | bed rail | chair arm | toilet seat | keyboard wrist rest | bathroom rail |
| 5 | N | N | N | N | N | N |
| 6 | N | N | N | N | N | N |
| 7 | N | N | N | N | N | N |
| 8 | N | N | N | N | N | N |

A second field trial was conducted in a hospital using formulations 1-8, a commercially available formulation (DAZO® fluorescent marking gel, Ecolab), and an inventive marking composition based on formulation 4 further comprising a preservative and a second surfactant. Each formulation or composition was tested on four HTOs. The second field trial was carried out in the same way as previously described, with the only difference being the disinfectant solution used to clean the surfaces. Here, a microfiber cloth saturated with EnCompass® quaternary disinfectant cleaner was wiped across the surface of the HTO after the formulations had been applied and allowed to dry. EnCompass® is commercially available from Ecolab Inc.

As before, the only formulation that was not fluorescent was formulation 7, which lacked a fluorescent component. Formulations 1, 2, and 8 were found to leave ghost marks on a table. Dazo® fluorescent marking gel was found to leave ghost marks on both a table and a bed rail. Note that these formulations contained a fluorescent monomer (Formulation 1, 2, and 8) or an optical brightener (Dazo® fluorescent marking gel) but not a fluorescent polymer. Formulations 3, 4, 5, and 6 comprising fluorescent polymers of the invention did not leave ghost marks on any of the high touch objects in this trial. This field trial provides additional data showing the utility of fluorescent polymers to overcome the problem of ghost marks observed with known fluorescent marking compositions. Also, better results were obtained with fluorescent polymers in formulations 3, 4, 5, and 6 and the inventive marking composition as compared to formulation 8, which was a mixture of a fluorescent monomer and a non-fluorescent polymer. The results of field trial 2 are shown in Table 6, wherein N indicates no ghost marks were observed and G indicates that ghost marks were observed.

TABLE 6

Results of Field Trial 2

| Formulation No. | High Tough Object | | | |
|---|---|---|---|---|
| | table | bed rail | toilet seat | bathroom rail |
| 1 | G | N | N | N |
| 2 | G | N | N | N |
| 3 | N | N | N | N |
| 4 | N | N | N | N |
| 5 | N | N | N | N |
| 6 | N | N | N | N |
| 7 | N | N | N | N |
| 8 | G | N | N | N |
| Dazo ® marking gel[1] | G | G | N | N |
| Inventive marking composition[2] | N | N | N | N |

[1]Commercially available Dazo ® fluorescent marking gel (Ecolab) was used as a comparative example. Dazo ® is an aqueous solution comprising a fluorescent stilbene-type optical brightener (D-282 UV-Blue; Day-Glo Corporation);
[2]Inventive marking composition based on formulation 4, further comprising a preservative and a second surfactant.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and processes without departing from the scope of the invention, it is intended that all matter contained in the above description shall be interpreted as illustrative and not in a limiting sense.

What is claimed is:

1. A method for evaluating cleaning of a surface, the method comprising:
   applying an amount of indicator material to the surface within a space, the indicator material comprising a water-dispersible fluorescent polymer from polymerization of one or more polymerizable fluorescent monomer units and one or more polymerizable non-fluorescent monomer units and having a weight average molecular weight of 2 to 2000 kDa;
   allowing for the surface to be cleaned; and
   determining if any of the indicator material remains on the surface by exposing the surface to UV radiation.

2. The method of claim 1, wherein the surface is a surface of a High Touch Object (HTO).

3. The method of claim 2, wherein the HTO is selected from the group consisting of a toilet handle, a toilet set, a bedpan flushing device, a faucet handle, a doorknob, a door handle, a push plat, a grab plate, a toilet area grab bar, a telephone receiver, a call button, a table, a chair seat, a chair arm, a bedrail, a drape, a room light switch, a computer mouse, a keyboard wrist rest, and a soap dispenser.

4. The method of claim 1, wherein the surface is a surface in a hospital, a nursing home, long-term care facility, clinic, doctor's office, or dental office.

5. The method of claim 1, wherein the surface is a surface in a restaurant, bar, nightclub, grocery store, hotel, bank, spa, health club, fitness center, locker room, day care center, indoor playground, school, convention center, office building, public restroom, movie theater, place of worship, public transit vehicle, airplane, taxicab, cruise ship, or ferry.

6. The method of claim 1, wherein the indicator material is applied with an applicator comprising a spray applicator, a foam pad applicator, a felt tip applicator, a brush, a roll, a wipe, or a solid form.

7. The method of claim 1, wherein the indicator material is applied with an applicator comprising a bottle or ampule.

8. The method of claim 1 further comprising recording a result of the evaluation and tracking cleaning outcomes.

9. The method of claim 8, wherein the recording is done using a mobile application.

10. The method of claim 8, wherein the result is stored as data.

11. The method of claim 10, wherein the data is wirelessly transmitted.

12. The method of claim 10, wherein the data is aggregated and analyzed.

13. The method of claim 10 further comprising using the data to assess whether cleaning activities are consistent with nosocomial infection control efforts.

14. The method of claim 10 further comprising preparing a report on the data.

15. The method of claim 14, wherein the report comprises a percentage of High Touch Objects (HTOs) cleaned, a comparison against baseline data, an identification of areas for improvement, or a combination thereof.

16. The method of claim 1, wherein the polymerizable fluorescent monomer unit has structure (I), (II) or (III):

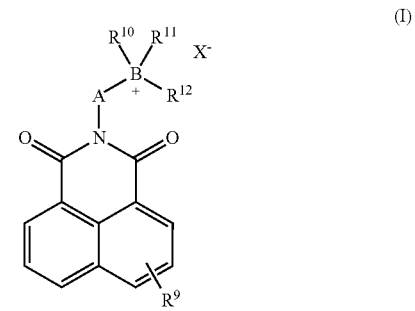

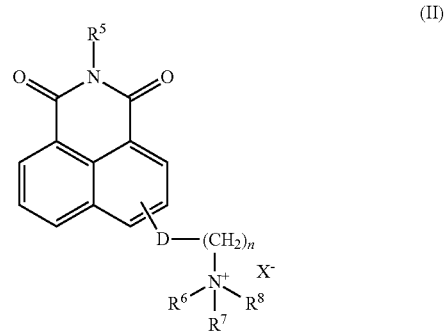

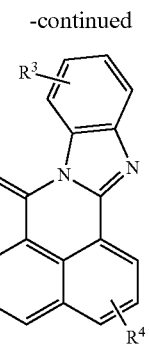

(III)

wherein:
n is an integer from 1 to 10;
A is alkyl, alkoxyalkyl, alkylamidoalkyl, aryl, or is absent; with the proviso that when A is absent, B is nitrogen and B is bonded directly to the imide nitrogen;
B is sulfur or nitrogen with the proviso that when B is sulfur, only one of $R^{10}$ or $R^{11}$ is present;
D is oxygen, nitrogen, sulfur or is absent, with the proviso that when D is absent, $(CH_2)_n$ is bonded directly to a carbon on the ring;
$R^3$ and $R^4$ are each independently sulfonic acid or a salt thereof, carboxylic acid or a salt thereof, allyloxy or vinylbenzyloxy, with the proviso that when one of $R^3$ or $R^4$ is sulfonic acid or a salt thereof or carboxylic acid or a salt thereof, the other must be allyloxy or vinylbenzyloxy;
$R^5$ is alkyl, alkylamino, hydroxyalkyl or allyl;
$R^6$ and $R^7$ are each independently alkyl;
$R^8$ is allyl, alkyl, vinylbenzyl or 2-hydroxy-3-allyloxypropyl;
$R^9$ is hydrogen, alkyl, alkoxy, halogen, sulfonic acid or a salt thereof, phosphonic acid or a salt thereof, dialkylamino, allyloxy or vinylbenzyloxy;
$R^{10}$ and $R^{11}$ are each independently alkyl;
$R^{12}$ is allyl, 2-hydroxy-3-allyloxypropyl, vinylbenzyl, 3-methacrylamidopropyl, 3-acrylamidopropyl, 2-acryloxyethyl or 2-methacryloxyethyl; and
$X^{31}$ is an anion.

17. The method of claim 16, wherein
the polymerizable fluorescent monomer unit has the structure (I) and is 4-methoxy-N-(3-N', N'-dimethylaminopropyl)naphthalimide vinyl benzyl chloride quaternary salt, or 4-methoxy-N -(3-N',N'-dimethylaminopropyl) naphthalimide 2-hydroxy-3-allyloxypropyl chloride quaternary salt; 4-methoxy-N-(3-N',N'-dimethylaminopropyl)naphthalimide allyl chloride quaternary salt;
the polymerizable fluorescent monomer unit has the structure (II) and is N-allyl-4-(2-N',N'-dimethylaminoethoxy)naphthalimide methyl sulfate quaternary salt; or
the polymerizable fluorescent monomer unit has the structure (III) and is 5-allyloxy-4'-carboxy -1,8-naphthoylene-1',2'-benzimidazole or 6-vinylbenzyloxy-4'-carboxy-1,8-naphthoylene-1',2'-benzimidazole.

18. The method of claim 16, wherein the polymer is a random polymer of a fluorescent monomer unit and polymerizable monomer units (Q), (W), and optionally (S), wherein the polymer has a formula $G_aQ_jW_t$, $G_aQ_vW_fS_c$, or a combination thereof, wherein:

G is the polymerizable fluorescent monomer unit;
Q is acrylic acid or a salt thereof, methacrylic acid or a salt thereof, maleic acid or a salt thereof, crotonic acid or a salt thereof, maleic anhydride, acrylamide, or acrylamidomethylpropane sulfonic acid or a salt thereof;
S is N-sulfomethacrylamide or N-sulfoethylacrylamide;
W is acrylic acid or a salt thereof, methacrylic acid or a salt thereof, itaconic acid or a salt thereof, maleic acid or a salt thereof, maleic anhydride, crotonic acid or a salt thereof, acrylamide, methacrylamide, vinyl sulfonic acid, styrene sulfonate, N-tert-butylacrylamide, N-isopropylacrylamide, N-butoxymethylacrylamide, N,N-dimethylacrylamide, N,N-diethylacrylamide, dimethylaminoethyl acrylate methyl chloride quaternary salt, dimethylaminoethyl acrylate benzyl chloride quaternary salt, dimethylaminoethyl acrylate methyl sulfate quaternary salt, dimethylaminoethyl methacrylate methyl sulfate quaternary salt, dimethylaminoethyl acrylamide methyl sulfate quaternary salt, dimethylaminopropyl acrylamide methyl sulfate quaternary salt, dimethylaminopropyl methacrylamide methyl sulfate quaternary salt, diallyldimethylammonium chloride, N-vinylformamide, a dimethylaminoethyl methacrylate acid salt, dimethylaminoethyl methacrylate methyl chloride quaternary salt, dimethylaminoethyl methacrylate benzyl chloride quaternary salt, methacrylamidopropyl trimethylammonium chloride, acrylamidopropyl trimethylammonium chloride, N,N'-methylene bisacrylamide, triallylamine, an acid salt of triallylamine, ethylene glycol dimethacrylate, 2-(hydroxymethyl)acrylic acid, 2-hydroxyethyl acrylate, 2-hydroxypropyl acrylate, 2-hydroxypropyl methacrylate, diethylene glycol dimethacrylate, triethylene glycol dimethacrylate, polyethylene glycol dimethacrylate, glycidyl methacrylate, 2-acrylamido2-methylpropane sulfonic acid or a salt thereof, vinyl alcohol, vinyl acetate, or N-vinylpyrrolidone, with the proviso that Q and W cannot both be the same;
a is from about 0.001 to about 10 mole percent;
c is from about 1 to about 40 mole percent;
f is from about 1 to about 97.999 mole percent;
j is from 0 to about 99.999 mole percent;
t is from 0 to about 99.999 mole percent;
v is from 0 to about 97.999 mole percent;
the sum of a, j and t equals 100 mole percent; and
the sum of a, v, f and c equals 100 mole percent.

19. The method of claim 17, wherein the polymer has the formula $G_aQ_jW_t$ or $G_aQ_vW_fS_c$ and wherein Q is acrylic acid; the polymer has the formula $G_aQ_jW_t$ and wherein Q is acrylic acid and W is acrylamide; the polymer has the formula $G_aQ_jW_t$ and wherein Q is acrylic acid and W is 2-acrylamido-2-methylpropane sulfonic acid; or the polymer has the formula the $G_aQ_vW_fS_c$ and wherein Q is acrylic acid, W is acrylamide, and S is N-sulfomethylacrylamide.

20. The method of claim 1, wherein the polymerizable fluorescent monomer unit has structure (IV) or (V):

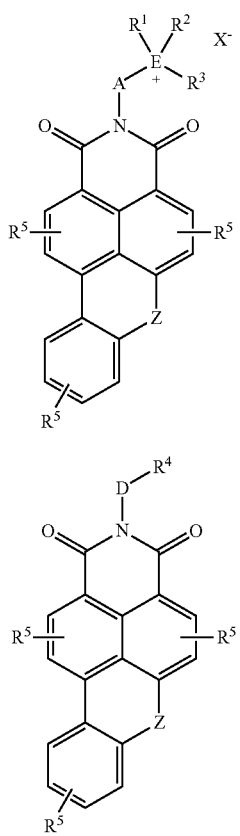

(IV)

(V)

wherein:
A is alkyl, alkoxyalkyl, alkylamidoalkyl, aryl, or is absent; with the proviso that when A is absent, E is nitrogen and E is bonded directly to the imide nitrogen;
E is sulfur or nitrogen with the proviso that when E is sulfur, only one of $R^1$ or $R^2$ is present;
D is alkyl, alkoxyalkyl, alkoxy, alkylamidoalkyl, alkylamino, NH, aryl or is absent;
R is independently hydrogen or alkyl;
$R^1$ and $R^2$ are each independently alkyl;
$R^3$ is allyl, 2-hydroxy-3-allyoxypropyl, vinyl benzyl, 3-methacrylamidopropyl, 3-acrylamidopropyl, 2-acryloxyethyl or 2-methacryloxyethyl;
$R^4$ is allyl, acryl, methacryl, 2-hydroxy-3-allyloxypropyl, vinyl benzyl, 2-acryloxyethyl and 2-methacryloxyethyl;
each $R^5$ is independently hydrogen, halogen, —$NO_2$, —C(O)OH or a salt thereof, —PO(OH)$_2$ or a salt thereof, —$SO_2$(OH) or a salt thereof, or —$SO_2$(NR$^2$);
$X^-$ is an anion; and
Z is —$CH_2$—, —C(O)—, —$CR_2$—, —NR—, —$NR_2^+$—, —N(OH)—, —O—, —S—, —S(O)—, or —$SO_2$—.

21. The method of claim 20, wherein
the polymerizable fluorescent monomer unit has the structure (IV) and is sulfonated-N-(3-N',N'-dimethylaminopropyl)benzo (k,l) xanthene-3,4-dicarboxylic imide 2-hydroxy-3-allyloxypropyl quaternary salt, sulfonated-N-(3-N',N'-dimethylaminopropyl)benzo (k,l) xanthene-3,4-dicarboxylic imide vinyl benzyl chloride quaternary salt, or sulfonated-N-(3-N',N'-dimethylaminopropyl)benzo (k,l) xanthene-3,4-dicarboxylic imide allyl chloride quaternary salt; or the polymerizable fluorescent monomer unit has structure (V) and is N-(3-N',N'-dimethylaminopropyl)benzo (k,l) xanthene-3,4-dicarboxylic imide allyl chloride quaternary salt.

22. The method of claim 1, wherein the polymerizable fluorescent monomer unit has structure (VI) or (VII):

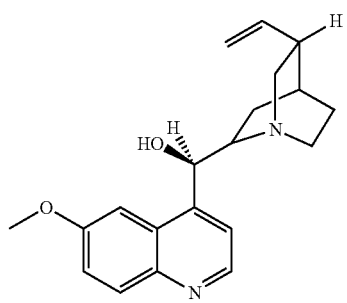

(VI)

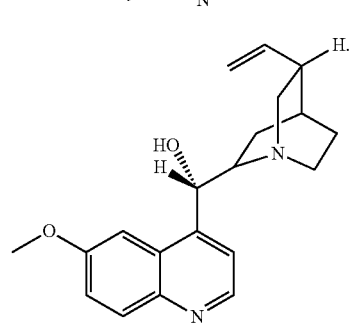

(VII)

23. The method of claim 1, wherein the polymerizable fluorescent polymer has been derived from polymerization of acrylic acid, 2-acrylamido-2-methylpropane sulfonic acid, and 4-methoxy-N-(3-N',N'-dimethylaminopropyl)-naphthalimide 2-hydroxy-3-allyloxypropyl quaternary salt.

24. The method of claim 1, wherein the polymerizable fluorescent monomer unit has structure (VIII) or (IX):

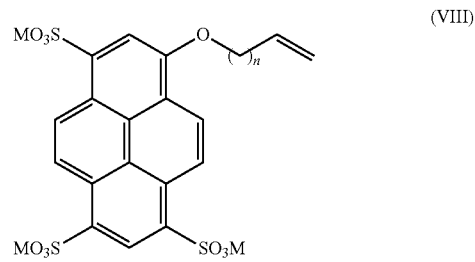

(VIII)

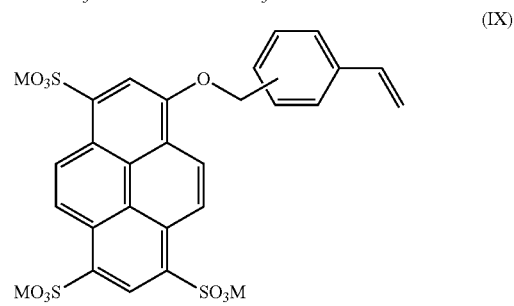

(IX)

wherein:
M is hydrogen, sodium, potassium, cesium, rubidium, lithium or ammonium; and n is an integer 1, 2, 3, 4, 6, or 9.

25. The method of claim 24, wherein
the polymerizable fluorescent monomer unit having structure (VIII) 8-(allyloxy)-1,3,6-pyrene trisulfonic acid or a sodium, potassium, cesium, rubidium, lithium or ammonium salt thereof; or
the polymerizable fluorescent monomer unit having structure (IX) is 8-(3-vinylbenzyloxy)-1,3,6-pyrene trisulfonic acid, 8-(4-vinylbenzyloxy)-1,3,6-pyrene trisulfonic acid, or a sodium, potassium, cesium, rubidium, lithium or ammonium salt thereof.

26. The method of claim 24, wherein the polymer is a random polymer of a polymerizable fluorescent monomer unit (G) and polymerizable monomer units (B), (C), and (D), wherein the polymer has a formula $G_xB_y$, $G_xB_jC_k$, $G_xB_mD_q$, $G_xB_rC_sD_t$, or a combination thereof wherein:
B is an acrylic acid or a salt thereof, methacrylic acid or a salt thereof, maleic acid or a
salt thereof, maleic anhydride, acrylamide, crotonic acid or a salt thereof, or a combination thereof;
C is methacrylic acid or a salt thereof, maleic acid or a salt thereof, maleic anhydride, crotonic acid or a salt thereof, itaconic acid or a salt thereof, acrylamide, methacrylamide, 2-acrylamido-2-methylpropanesulfonic acid or a salt thereof, polyethylene glycol monomethacrylate, vinyl phosphonic acid or a salt thereof, styrene sulfonic acid or a salt thereof, vinyl sulfonic acid or a salt thereof, 3-allyloxy-2-hydroxypropane sulfonic acid or a salt thereof, N-alkyl (meth)acrylamide, t-butyl (meth)acrylate, N-alkyl (meth)acrylate, N-alkanol-Nalkyl(meth)acrylate, vinyl acetate, 2-hydroxy N-alkyl(meth)acrylate, alkyl vinyl ether, alkoxyethyl acrylate, N-alkanol (meth)acrylamide, N,N-dialkyl(meth)acrylamide, 1-vinyl-2-pyrrolidinone, or a combination thereof;
D is sulfomethylacrylamide or sulfoethylacrylamide;
G is the fluorescent monomer unit;
j is from about 1 to about 98 mol %;
k is from about 1.999 to about 98 mol %;
m is from about 1 to about 95 mol %;
q is from about 4.999 to about 40 mol %;
r is from about 1 to about 89.999 mol %;
s is from about 1 to about 89.999 mol %;
t is from about 5 to about 40 mol %;
x is from about 0.001 to about 1 mol %;
y is from about 99.000 to about 99.999 mol %;
the sum of x and y equals 100 mol %;
the sum of x, j and k equals 100 mol %;
the sum of x, m and q equals 100 mol %; and
the sum of x, r, s and t equals 100 mol %.

27. The method of claim 26, wherein
the polymer has the formula $G_xB_y$ wherein B is acrylic acid or a salt thereof;
the polymer has the formula $G_xB_jC_k$ wherein B is acrylic acid or a salt thereof, and C is acrylamide;
the polymer has the formula $G_xB_mD_q$ wherein B is acrylic acid or a salt thereof, and D is sulfomethylacrylamide; or
the polymer has the formula $G_xB_rC_sD_t$ wherein B is acrylic acid or a salt thereof, C is acrylamide, and D is sulfomethylacrylamide.

28. The method of claim 1, wherein the indicator material is in a composition that does not further comprise a fluorescent dye encapsulated by, coated with, or entrapped within a nonfluorescent polymer; or a fluorescent dye covalently linked to a non-fluorescent polymer in an amount sufficient to leave a mark on a surface to which the composition is applied after removal of the composition from the surface.

29. The method of claim 1, wherein the indicator material is in a composition that does not further comprise a fluorescent dye encapsulated by, coated with, or entrapped within a nonfluorescent polymer; or a fluorescent dye covalently linked to a non-fluorescent polymer.

30. The method of claim 1, wherein the indicator material is in a composition that comprises about 8 to about 16 wt. % of the fluorescent polymer; from about 1 to about 6 wt. % of and amphoteric surfactant; from about 0.1 to about 0.4 wt. % of a thickener; from about 0.1 to about 0.7 wt. % of a preservative; and from about 67 to about 91 wt. % of solvent.

31. The method of claim 1, wherein the indicator material has a light absorption spectrum in the range of about 310 to about 400 nm, and light emission spectrum in the range of about 400 to about 750 nm upon exposure to UV radiation.

32. The method of claim 1, wherein the indicator material has a light absorption spectrum in the range of about 365 to about 395 nm, and light emission spectrum in the range of about 410 to about 700 nm upon exposure to UV radiation.

33. The method of claim 1, wherein indicator material has the viscosity of a water-thin liquid.

34. The method of claim 1, wherein the indicator material has a viscosity from about 10 to about 6,000 centipoise when measured with a Brookfield LVT viscometer at 25° C. with a #1 spindle at 60 rpm.

35. The method of claim 1, wherein the indicator material has a viscosity from about 20 to about 200 centipoise when measured with a Brookfield LVT viscometer at 25° C. with a #1 spindle at 60 rpm.

36. The method of claim 1, wherein the indicator material is applied with an applicator comprising a plastic squeeze bottle with a foam pad attached to the end.

37. The method of claim 1, wherein the indicator material is inconspicuous, transparent, opaque, or semi-opaque before it is applied to the surface.

38. The method of claim 1, wherein the indicator material is inconspicuous, transparent, opaque, or semi-opaque on the surface.

39. The method of claim 1, wherein the indicator material is allowed to dry on the surface.

40. The method of claim 1, wherein the indicator material does not leave behind a residual fluorescent mark when the indicator material is removed during a cleaning process.

41. A kit for evaluating cleaning of a surface, the kit comprising:
an applicator;
an indicator material comprising a water-dispersible fluorescent polymer from polymerization of one or more polymerizable fluorescent monomer units and one or more polymerizable non-fluorescent monomer units and having a weight average molecular weight of 2 to 2000 kDa; and
a portable ultraviolet light emitting light source.

42. The kit of claim 41, wherein the applicator is selected from the group consisting of a spray applicator, a foam pad applicator, a felt tip applicator, a brush, a roll, a wipe, a solid form, or a plastic squeeze bottle with a foam pad attached to the end.

43. The kit of claim 41, wherein the applicator is a bottle or ampule.

44. The kit of claim 41, wherein the applicator is a spray applicator.

45. The kit of claim 41, the kit further comprising a mobile application.

46. The kit of claim 41, wherein the portable ultraviolet light emitting light source emits light having a wavelength range of from about 310 to about 400 nm.

* * * * *

UNITED STATES PATENT AND TRADEMARK OFFICE
CERTIFICATE OF CORRECTION

PATENT NO. : 10,155,058 B2
APPLICATION NO. : 15/829006
DATED : December 18, 2018
INVENTOR(S) : Wegner et al.

It is certified that error appears in the above-identified patent and that said Letters Patent is hereby corrected as shown below:

In the Claims

Column 30, Line 2, Claim 3: "a push plat," should read --a push plate,--

Column 31, Line 47, Claim 16: "$X^{31}$ is an anion." should read --$X^-$ is an anion.--

Column 31, Line 50, Claim 17: "4-methoxy-N-(3-N', N'-dimethylamino-" should read --4-methoxy-N-(3-N',N'-dimethylamino- --

Column 31, Line 52, Claim 17: "4-methoxy-N -(3-N',N'-dimethylaminopropyl)" should read --4-methoxy-N-(3-N',N'-dimethylaminopropyl)--

Column 31, Line 60, Claim 17: "4'-carboxy -1,8-naph-" should read --4'-carboxy-1,8-naph- --

Column 31, Line 66, Claim 18: "formula $G_aQ_jW_t$, $G_aQ_vW_f\,S_c$, or r" should read --formula $G_aQ_jW_t$, $G_aQ_vW_f\,S_c$, or--

Column 32, Line 42, Claim 18: "2-acrylamido2-" should read --2-acrylamido-2--

Column 32, Line 58, Claim 19: "method of claim 17," should read --method of claim 18,--

Column 33, Line 54, Claim 20: "thereof, -S02 (OH) or a salt thereof, or -S02 (NR2);" should read --thereof, –$SO_2(OH)$ or a salt thereof, or –$SO_2(NR^2)$;--

Column 35, Line 7, Claim 25: "(VIII) 8-(allyloxy)-1,3,6-pyrene" should read --(VIII) is 8-(allyloxy)-1,3,6-pyrene--

Column 35, Line 34, Claim 26: "N-alkanol-Nalkyl(meth)acrylate," should read --N-alkanol-N-alkyl(meth)acrylate,--

Signed and Sealed this
Twenty-first Day of April, 2020

Andrei Iancu
*Director of the United States Patent and Trademark Office*